(12) United States Patent
Drake et al.

(10) Patent No.: US 10,329,617 B2
(45) Date of Patent: Jun. 25, 2019

(54) COMPOSITIONS AND METHODS FOR MODULATING AN IMMUNE RESPONSE

(71) Applicant: THE JOHNS HOPKINS UNIVERSITY, Baltimore, MD (US)

(72) Inventors: Charles G. Drake, Baltimore, MD (US); Drew M. Pardoll, Brookeville, MD (US); Jonathan D. Powell, Baltimore, MD (US); Derese Getnet, Baltimore, MD (US); Edward L. Hipkiss, Baltimore, MD (US); Joseph F. Grosso, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 171 days.

(21) Appl. No.: 15/178,028

(22) Filed: Jun. 9, 2016

(65) Prior Publication Data

US 2016/0354464 A1 Dec. 8, 2016

Related U.S. Application Data

(60) Division of application No. 14/282,338, filed on May 20, 2014, now Pat. No. 9,523,126, which is a continuation of application No. 12/991,654, filed as application No. PCT/US2009/002872 on May 8, 2009, now abandoned.

(60) Provisional application No. 61/126,882, filed on May 8, 2008.

(51) Int. Cl.

| | | |
|---|---|---|
| *C07H 21/04* | (2006.01) | |
| *C12Q 1/6881* | (2018.01) | |
| *C07K 14/47* | (2006.01) | |
| *C12N 15/113* | (2010.01) | |
| *G01N 33/50* | (2006.01) | |
| *A61K 39/00* | (2006.01) | |
| *A61K 39/39* | (2006.01) | |
| *C12N 15/117* | (2010.01) | |

(52) U.S. Cl.
CPC ........ *C12Q 1/6881* (2013.01); *A61K 39/0011* (2013.01); *A61K 39/39* (2013.01); *C07K 14/4702* (2013.01); *C12N 15/113* (2013.01); *C12N 15/117* (2013.01); *G01N 33/5011* (2013.01); *A61K 2039/55561* (2013.01); *A61K 2039/572* (2013.01); *C12N 2310/14* (2013.01); *C12N 2310/17* (2013.01); *C12N 2320/31* (2013.01); *C12Q 2600/136* (2013.01)

(58) Field of Classification Search
CPC .................................................. C12N 15/111
See application file for complete search history.

(56) References Cited

U.S. PATENT DOCUMENTS

| | | |
|---|---|---|
| 4,305,872 A | 12/1981 | Johnston |
| 4,316,891 A | 2/1982 | Guillemin |
| 5,270,163 A | 12/1993 | Gold |
| 5,496,938 A | 3/1996 | Gold |
| 5,567,588 A | 10/1996 | Gold |
| 5,637,459 A | 6/1997 | Burke |
| 5,656,611 A | 8/1997 | Kabanov |
| 5,660,985 A | 8/1997 | Pieken |
| 5,672,695 A | 9/1997 | Eckstein |
| 5,683,867 A | 11/1997 | Biesecker |
| 5,698,687 A | 12/1997 | Eckstein |
| 5,705,337 A | 1/1998 | Gold |
| 5,707,796 A | 1/1998 | Gold |
| 5,753,613 A | 5/1998 | Ansell |
| 5,763,177 A | 6/1998 | Gold |
| 5,785,992 A | 7/1998 | Ansell |
| 5,817,635 A | 10/1998 | Eckstein |
| 5,861,254 A | 1/1999 | Schneider |
| 5,958,691 A | 9/1999 | Pieken |
| 6,011,020 A | 1/2000 | Gold |
| 6,051,698 A | 4/2000 | Janjic |
| 6,120,798 A | 9/2000 | Allen |
| 6,221,959 B1 | 4/2001 | Kabanov |
| 6,346,613 B1 | 2/2002 | O'Mahony |
| 6,353,055 B1 | 3/2002 | Kabanov |
| 2003/0003469 A1 | 1/2003 | Stinchcomb |
| 2005/0130265 A1* | 6/2005 | Georgopoulos ... A01K 67/0276 435/69.1 |

FOREIGN PATENT DOCUMENTS

| | | |
|---|---|---|
| EP | 0812912 | 12/1997 |
| WO | 1991019813 | 12/1991 |
| WO | 1992001065 | 1/1992 |
| WO | 1992005285 | 4/1992 |
| WO | 1992014843 | 9/1992 |
| WO | 1993023569 | 11/1993 |
| WO | 1995006731 | 3/1995 |
| WO | 1995011910 | 5/1995 |
| WO | 1998018480 | 5/1998 |
| WO | 2009046104 | 4/2009 |

OTHER PUBLICATIONS

Sugimoto et al. ("Foxp3-dependent and-independent molecules specific for CD25+ CD4+ natural regulatory T cells revealed by DNA microarray analysis." International immunology 18.8 (2006): 1197-1209).*
Ma et al (1993) Design and synthesis of RNA miniduplexes via a synthetic linker approach. 2. Generation of covalently closed, double-stranded cyclic HIV-1 TAR RNA analogs with high Tat-binding affinity. Nucleic Acids Res. Jun. 11, 1993;21(11)2585-9.
Ma et al (1993) Design and synthesis of RNA miniduplexes via a synthetic linker approach. Biochemistry. Feb. 23, 1993;32(7)1751-8.

(Continued)

Primary Examiner — Kimberly Chong
(74) Attorney, Agent, or Firm — John Hopkins Technology Ventures

(57) ABSTRACT

The invention generally features compositions and methods for modulating an immune response. In particular embodiments, such compositions and methods modulate regulatory T cell suppressive activity.

18 Claims, 3 Drawing Sheets

Specification includes a Sequence Listing.

(56) References Cited

OTHER PUBLICATIONS

Cload et al (1991) Polyether tethered oligonucleotide probes. J Am Chem Soc No. 113 (Jul. 1, 1991), pp. 6324-6326.
Jaschke et al (1993) Automated Incorporation of Polyethylene Glycol into. Synthetic Oligonucleotides. Tetrahedron Letters 34:301-304.
Ono et al (1991) DNA triplex formation of oligonucleotide analogs consisting of linker groups and octamer segments that have opposite sugar-phosphate backbone polarities. Biochemistry, 1991, 30 (41), pp. 9914-9921.
Ferentz et al (1991) J Am Chem Soc 113. Disulfide-crosslinked oligonucleotides. J. Am. Chem. Soc., 1991, 113 (10), pp. 4000-4002.
Ellington et al (1990) In vitro selection of RNA molecules that bind specific ligands. Nature. Aug. 30, 1990;346 (6287):818-22.
Froehler et al (1986) Synthesis of DNA via deoxynucleoside H-phosphonate intermediates. Nucleic Acids Res. Jul. 11, 1986;14(13):5399-407.
Froehler et al (1986) Deoxynucleoside H-Phosphonate diester intermediates in the synthesis of internucleotide phosphate analogues. Tet Lett 27:5575-5578.
Sood et al (1977) A rapid and convenient synthesis of polythymidylic acid by the modified triester approach. Nucleic Acids Res. Aug. 1977;4(8):2757-65.
Hirose et al (1978) Rapid synthesis of trideoxyribonucleotide blocks. Tet Lett 28:2449.
Merrifield et al (1963) Solid Phase Peptide Synthesis. I. The Synthesis of a Tetrapeptide. J. Am. Chem. Soc., 1963, 85(14), pp. 2149-2154.
Durand et al (1990) Circular dichroism studies of an oligodeoxyribonucleotide containing a hairpin loop made of a hexaethylene glycol chain: conformation and stability. Nucleic Acids Res. Nov. 11, 1990;18(21):6353-9.
Marki et al (1981) Total solid-phase synthesis of porcine gut gastrin releasing peptide (GRP), a mammalian bombesin. J. Am. Chem. Soc., 1981, 103 (11), pp. 3178-3185.
Cayouette et al (1997) Adenovirus-mediated gene transfer of ciliary neurotrophic factor can prevent photoreceptor degeneration in the retinal degeneration (rd) mouse. Hum Gene Ther. Mar. 1, 1997;8(4):423-30.
Seela et al (1987) Oligodeoxyribonucleotides containing 1,3-propanediol as nucleoside substitute. Nucleic Acids Res. Apr. 10, 1987;15(7):3113-29.
Bloomer et al (1997) Highly efficient and sustained gene transfer in adult neurons with a lentivirus vector. J Virol. Sep. 1997;71(9):6641-9.
Richardson et al (1991) Tethered oligonucleotide probes. A strategy for the recognition of structured RNA. J AM Chem Soc No. 113 (Jun. 1, 1991), pp. 5109-5111.
Miyoshi et al (1997) Stable and efficient gene transfer into the retina using an HIV-based lentiviral vector. Proc Natl Acad Sci U S A. Sep. 16, 1997;94(19):10319-23.
Wadler et al (1990) Antineoplastic activity of the combination of interferon and cytotoxic agents against experimental and human malignancies: a review. Cancer Res. Jun. 15, 1990;50(12):3473-86.
Pillai et al (2007) Transient regulatory T-cells: a state attained by all activated human T-cells. Clin Immunol. Apr. 2007;123(1):18-29. Epub Dec. 19, 2006.
Wang et al (2007) Transient expression of FOXP3 in human activated nonregulatory CD4+ T cells. Eur J Immunol. Jan. 2007;37(1):129-38.
Zhang et al (2007) Expression of a non-DNA-binding isoform of Helios induces T-cell lymphoma in mice. Blood. Mar. 1, 2007;109(5):2190-7. Epub Nov. 16, 2006.
Hahm et al (1998) Helios, a T cell-restricted Ikaros family member that quantitatively associates with Ikaros at centromeric heterochromatin. Genes Dev. Mar. 15, 1998;12(6):782-96.
Tone et al (2008) Smad3 and NFAT cooperate to induce Foxp3 expression through its enhancer. Nat Immunol. Feb. 2008;9(2):194-202. Epub Dec. 23, 2007.
Thornton et al (1998) CD4+CD25+ immunoregulatory T cells suppress polyclonal T cell activation in vitro by inhibiting Interleukin 2 production. J Exp Med. Jul. 20, 1998;188(2):287-96.
Ono et al (2007) Foxp3 controls regulatory T-cell function by interacting with AML1/Runx1. Nature. Apr. 5, 2007;446 (7136):685-9. Epub Mar. 21, 2007.
Liu et al (2005) Cooperation of invariant NKT cells and CD4+CD25+ T regulatory cells in the prevention of autoimmune myasthenia. J Immunol. Dec. 15, 2005;175(12):7898-904.
von Boehmer et al (2005) Mechanisms of suppression by suppressor T cells. Nat Immunol. Apr. 2005;6(4):338-44.
Sakaguchi et al (1995) Immunologic self-tolerance maintained by activated T cells expressing IL-2 receptor alpha-chains (CD25). Breakdown of a single mechanism of self-tolerance causes various autoimmune diseases. J Immunol. Aug. 1, 1995;155(3):1151-64.
Shevach et al (2004) Regulatory/suppressor T cells in health and disease. Arthritis Rheum. Sep. 2004;50(9)2721-4.
Curiel et al (2004) Specific recruitment of regulatory T cells in ovarian carcinoma fosters immune privilege and predicts reduced survival. Nat Med. Sep. 2004;10(9):942-9. Epub Aug. 22, 2004.
Liyanage et al (2002) Prevalence of regulatory T cells is increased in peripheral blood and tumor microenvironment of patients with pancreas or breast adenocarcinoma. J Immunol. Sep. 1, 2002;169(5)2756-61.
Fontenot et al (2005) Regulatory T cell lineage specification by the forkhead transcription factor foxp3. Immunity. Mar. 2005;22(3):329-41.
Drake et al (2006) Mechanisms of immune evasion by tumors. Adv Immunol. 2006;90:51-81.
Terabe et al (2004) Immunoregulatory T cells in tumor immunity. Curr Opin Immunol. Apr. 2004;16(2):157-62.
North et al (1982) Cyclophosphamide-facilitated adoptive immunotherapy of an established tumor depends on elimination of tumor-induced suppressor T cells. J Exp Med. Apr. 1, 1982;155(4):1063-74.
Berd et al (1982) Augmentation of the human immune response by cyclophosphamide. Cancer Res. Nov. 1982;42 :11):4862-6.
Berd et al (1986) Induction of cell-mediated immunity to autologous melanoma cells and regression of metastases after treatment with a melanoma cell vaccine preceded by cyclophosphamide. Cancer Res. May 1986;46(5):2572-7.
Nigam et al (1998) Immunomodulatory properties of antineoplastic drugs administered in conjunction with GM-CSF-secreting cancer cell vaccines. Int J Oncol. Jan. 1998;12(1):161-70.
Machiels et al (2001) Cyclophosphamide, doxorubicin, and paclitaxel enhance the antitumor immune response of granulocyte/macrophage-colony stimulating factor-secreting whole-cell vaccines in HER-2/neu tolerized mice. Cancer Res. May 1, 2001;61(9):3689-97.
Drake et al (2005) Androgen ablation mitigates tolerance to a prostate/prostate cancer-restricted antigen. Cancer Cell. Mar. 2005;7(3):239-49.
Sugimoto et al (2006) Foxp3-dependent and -independent molecules specific for CD25+CD4+ natural regulatory T ells revealed by DNA microarray analysis. Int Immunol. Aug. 2006;18(8):1197-209. Epub Jun. 13, 2006.
Wahl et al (1987) Molecular hybridization of immobilized nucleic acids: theoretical concepts and practical considerations. Methods Enzymol. 1987;152:399-407.
Kimmel et al (1987) Identification and characterization of specific clones: strategy for confirming the validity of presumptive clones. Methods Enzymol. 1987;152:507-11.
Hermann et al (2000) Adaptive recognition by nucleic acid aptamers. Science. Feb. 4, 2000;287(5454):820-5.
Grunstein et al (1975) Colony hybridization: a method for the isolation of cloned DNAs that contain a specific gene. Proc Natl Acad Sci U S A. Oct. 1975;72(10):3961-5.
Chu et al (2006) Aptamer mediated siRNA delivery. Nucleic Acids Res. Jun. 1, 2006;34(10):e73.
Tuschl et al (2001) RNA interference and small interfering RNAs. Chembiochem. Apr. 2, 2001;2(4):239-45.

(56) References Cited

OTHER PUBLICATIONS

Sharp et al (2001) RNA interference-2001. Genes Dev. Mar. 1, 2001;15(5):485-90.

Hutvagner et al (2002) RNAi: nature abhors a double-strand. Curr Opin Genet Dev. Apr. 2002;12(2):225-32.

Hannon et al (2002) RNA interference. Nature. Jul. 11, 2002;418(6894):244-51.

Brummelkamp et al (2002) A system for stable expression of short interfering RNAs in mammalian cells. Science. Apr. 19, 2002;296(5567):550-3. Epub Mar. 21, 2002.

Paddison et al (2002) Short hairpin RNAs (shRNAs) induce sequence-specific silencing in mammalian cells. Genes Dev. Apr. 15, 2002;16(8):948-58.

Paul et al (2002) Effective expression of small interfering RNA in human cells. Nat Biotechnol. May 2002;20(5):505-8.

Sui et al (2002) A DNA vector-based RNAi technology to suppress gene expression in mammalian cells. Proc Natl Acad Sci U S A. Apr. 16, 2002;99(8):5515-20.

Yu et al (2002) RNA interference by expression of short-interfering RNAs and hairpin RNAs in mammalian cells. Proc Natl Acad Sci U S A. Apr. 30, 2002;99(9):6047-52. Epub Apr. 23, 2002.

Miyagishi et al (2002) U6 promoter-driven siRNAs with four uridine 3' overhangs efficiently suppress targeted gene expression in mammalian cells. Nat Biotechnol. May 2002;20(5):497-500.

Lee et al (2002) Expression of small interfering RNAs targeted against HIV-1 rev transcripts in human cells. Nat Biotechnol. May 2002;20(5):500-5.

Reynolds et al (2004) Rational siRNA design for RNA interference. Nat Biotechnol. Mar. 2004;22(3):326-30. Epub Feb. 1, 2004.

Haseloff et al (1988) Simple RNA enzymes with new and highly specific endoribonuclease activities. Nature. Aug. 18, 1988;334(6183):585-91.

Rossi et al (1992) Ribozymes as anti-HIV-1 therapeutic agents: principles, applications, and problems. AIDS Res Hum Retroviruses. Feb. 1992;8(2):183-9.

Hampel et al (1989) RNA catalytic properties of the minimum (−)sTRSV sequence. Biochemistry. Jun. 13, 1989;28 :12):4929-33.

Hampel et al (1990) 'Hairpin' catalytic RNA model: evidence for helices and sequence requirement for substrate RNA. Nucleic Acids Res. Jan. 25, 1990;18(2):299-304.

Moore et al (1992) Site-specific modification of pre-mRNA: the 2'-hydroxyl groups at the splice sites. Science. May 15, 1992;256(5059):992-7.

Shabarova et al (1991) Chemical ligation of DNA: the first non-enzymatic assembly of a biologically active gene. Nucleic Acids Res. Aug. 11, 1991;19(15):4247-51.

Belton et al (1997) Amino-Linked Ribozymes:Post-Synthetic Conjugation of Half-Ribozymes. Nucleosides & Nucleotides 16:951-954.

Belton et al (1997) Post-synthetically Ligated Ribozymes: An Alternative Approach to Iterative Solid-Phase Synthesis. Bioconjugate Chem *:204-212.

Gold et al (1995) Diversity of oligonucleotide functions. Annu Rev Biochem. 1995;64:763-97.

Brody et al (2000) Aptamers as therapeutic and diagnostic agents. J Biotechnol. Mar. 2000;74(1):5-13.

Jayasena et al (1999) Aptamers: an emerging class of molecules that rival antibodies in diagnostics. Clin Chem. Sep. 1999;45(9):1628-50.

Kusser et al (2000) Chemically modified nucleic acid aptamers for in vitro selections: evolving evolution. J Biotechnol. Mar. 2000;74(1):27-38.

* cited by examiner

|  |  |  |  |  |  |  |
|---|---|---|---|---|---|---|
| 1 | metdaidgyi | tcdnelsper | ehsnmaidlt | sstpngqhas | pshmtstnsv | klemqsdeec |
| 61 | drkplsrene | irghdegssl | eepliessev | adnrkvqelq | geggirlpng | klk<u>cdvcgmv</u> |
| 121 | <u>cigpnvlmvh</u> | <u>krshtgerpf</u> | <u>hcnqcgasft</u> | <u>qkgnllrhik</u> | <u>lhsgekpfkc</u> | <u>pfcsyacrrr</u> |
| 181 | <u>daltghlrth</u> | svgkphk<u>cny</u> | <u>cgrsykqrss</u> | <u>leehkerchn</u> | <u>ylqnvsmeaa</u> | <u>gqvmshhvpp</u> |
| 241 | medckeqepi | mdnnislvpf | erpaviekli | gnmgkrksst | pqkfvgeklm | rfsypdihfd |
| 301 | mnltyekeae | lmqshmmdga | innaitylga | ealhplmqhp | pstiaevapv | issaysqvyh |
| 361 | pnrierpisr | etadshennm | dgpislirpk | srpqereasp | snscldstds | esshddhqsy |
| 421 | qqhpalnpkr | kqspaymked | vkaldttkap | kgslkdiykv | fngegeqira | fkcehorvlf |
| 481 | ldhvmytihm | gchgyrdple | cnicgyrsqd | ryefsshivr | gehtfh | (SEQ ID NO: 3) |

BLUE WITH UNDERLINE: DNA BINDING DOMAIN, RED SHADING: DIMERIZATION DOMAIN

REF. HOSOKAWA Y, MAEDA Y, AND SETO M (1999) HUMAN HELIOS, AN IKAROS-RELATED ZINC FINGER DNA BINDING PROTEIN:cDNA CLONING AND TISSUE EXPRESSION PATTERN. IMMUNOGENETICS (50):106-108

FIG. 3A

AAAGCCCTTTCCAATTTCTCTTCCCCAGGTCTGAAGCCAGTCTTGTAGAGGGCTGGAGTG
GTTGTTGGACGACTAGAACCCTGGGCTTTGCAGGGTGCTGGGAGCTGGAAGTCTTCACCA
TGGCCTGTCAGGAGAAGCCCCTGGGGGCTGGTCTACCATGCTGACCAGTGGTTGAATAGA
GTGCCTGCTGAGGTCAAGAGATGCAGCCGCCAATTCCTGGACAACCTAAAAGCCTCACAA
GCTTCAAGTCTCCAAGGACTCTCCAAATCCCAGGATCTCCCTGCCATCACATCCTAGAAT
TTAAAACCTGAGAACATCAAGTTCAGGAAAGCTTGGGGATTCAAAGCCCAGCACCAAAG
AAAGCGGGACCCACACTCGCCAGCTCTGTGATCTTGGGCAAGTTGCTTGACTACTTATAC
CTCCGTTTCCCTCATCTGTATAACAGGAATACAATAATGATGAGATGGAGCTCAAGGGGC
CATGGTGAGGATTGAACATGATCACTTGTGAGACATGTTCAGCACTGTATCTGACCCATG
CGAAAATTCAAGATAAACATCAGCTACTGAGATGATGGCCGGATATTTGGAATCCTAAATCC
TTGGAAACTGGGGCTTTTTGAAGTAAAAGACCCCAAAGGCTGAGGGCCTCAGAAGCATCA
GGCCATGATGTTCCTGAAACAAGAGGGTCAGGTCCCAATGGGCCTCTGGGGTTCATCGT
GAGGATGGATGCATTAATATTGGGGACCTGCTAGGGACCTTCCCAGTGGGACAGTGGCTG
GGTCAGGGCAACTCAAGCCCTAAAACGTGAGGCGAGACTTTCTCTCTTTCCTCATTC
AGTAACTGTCAGTAGATTCTGGGAGCCAGGGATTCTCCGACTCTTCAAGTCCATGAATTT
TAGGGGATGACAGTGGGCTCTCCGCTTTCTCCTCCATGAAGTAACTTACATGCCCCTCAC
CCTCTGTGGGAGGGGTGTTGCAGGGGGTGCAGAACTCCCCTCGCGGGTAGTTCAAGCAA
TGGGGACCATATCAATTCCATCTATAGGGAAACTGAGGCCTGGAGTAGGGCGAGGCCTCT
GGGAACCCAGCCCTATTCTGTCTCTTTCCCTGGCATTTCCCATCCACACATAGAGCTTCA
GATTCTCTTTCTTTCCCCAGAGACCTCAAATATCCTCTCACTCACAGAATGGTGTCTCT
GCCTGCCTCGGGTTGGCCCTGTGATTTATTTTAGTTCTTTTCCCTTGTTTTTTTTTTTC
AAACTCTATACACTTTTGTTTAAAAACTGTGGTTTCTCATGAGCCCTATTATCTCATTG
ATACCTCTCACCTCTGTGGTGACGGGAAGAAATCATATTTTCAGATGACTCGTAAAGGGC
AAAGAAAAAAACCCAAAATTTCAAAATTTCCGTTTAAGTCTCATAAGAAAAGGAGA
AACACAGAGAGAGAGAAAAAAAAAACTATGAGAACCCCCCCCACCCGTGATTATCAGC
GCACACACTCATCGAAAAAAATTTGGATTATTAGAAGAGAGAGGTCTGCGGCTTCCACAC
CGTACAGCGTGGTTTTTCTTCTCGGTATAAAAGCAAAGTTGTTTTTGATACGTGACAGTT
TCCCAC(⟶ TSS) (SEQ ID NO: 4)

HUMAN FoxP3 PROMOTER ACCESSION AF235097
RED: CORRESPONDING REGION TO MOUSE CELL LINE HELIOS CHIP TARGET

FIG. 3B

COMPOSITIONS AND METHODS FOR MODULATING AN IMMUNE RESPONSE

CROSS-REFERENCE TO RELATED APPLICATION

This application is a division of U.S. patent application No. Division of Ser. No. 14/282,338, filed May 20, 2014, which is a continuation of U.S. patent application Ser. No. 12/991,654, filed Nov. 8, 2010, and is a 35 U.S.C. § 371 U.S. national entry of International Application PCT/US2009/002872, having an international filing date of May 8, 2009, which claims the benefit of U.S. Provisional Application No. 61/126,882, filed May 8, 2008, the content of each of the aforementioned applications is herein incorporated by reference in their entirety.

STATEMENT OF RIGHTS TO INVENTIONS MADE UNDER FEDERALLY SPONSORED RESEARCH

This invention was made with government support under grant number CA098252, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Mar. 8, 2014, is named P10323-03_ST25.txt and is 18,804 bytes in size.

BACKGROUND OF THE INVENTION

Approximately 1 million Americans are diagnosed with neoplasia every year, and about half a million people in the United States die of the disease annually. While improvements in neoplasia detection, diagnosis, and treatment have increased the survival rate for many types of neoplasia, only about 60 percent of people diagnosed with neoplasia are alive five years after treatment, making neoplasia the second leading cause of death in the United States. Cancer vaccines are one promising approach to treating neoplasia through induction of an immune response against tumor-associated antigens (TAA). However, immunological tolerance against self-antigens may limit an effective antitumor immune response.

$CD4^+CD25^+$ regulatory T cells (Treg) function in maintaining a balance between immune tolerance and immune responsiveness. Treg suppress pathologic and physiological immune response, contributing to the maintenance of immunological self-tolerance and immune homeostasis. In conditions, such as chronic infection and neoplasia, Treg suppressive activity undesirably reduces the efficacy of an immune response capable of fighting the infection or eliminating the neoplasia. Conversely, in conditions where an immune response is undesirably activity, such as autoimmunity and inflammatory disease, Treg suppressive activity is inadequate to reduce the undesirable immune response. Conventional methods for modulating an immune response are inadequate for the treatment of such conditions. Methods for modulating Tregs suppressive activity are urgently required, not only for the treatment of neoplasia, but also for the treatment of chronic infection and inflammation.

SUMMARY OF THE INVENTION

As described below, the present invention features compositions and methods for modulating regulatory T cell suppressive activity for the treatment of neoplasia, chronic infection, pathogen infection, autoimmune disease, and inflammatory disease.

In one aspect, the invention generally provides a method for modulating $CD4^+CD25^+$ regulatory T cell (Treg) biological function, the method involving contacting the cell with an agent that alters Helios expression, thereby modulating $CD4^+CD25^+$ T cell biological function. In one embodiment, the method increases or reduces Treg suppressive activity, for example, by at least about 5%, 10%, 20%, 25%, 50%, 75%, or 100%.

In another aspect, the invention provides a method for increasing an effector T cell-mediated immune response, the method involving contacting the cell with an agent that reduces Helios expression or biological activity, thereby increasing the immune response. In one embodiment, the method reduces Treg suppression of an effector T cell mediated immune response. In another embodiment, the method reduces Treg suppressive activity or enhances an effector T cell-mediated immune response.

In another aspect, the invention provides a method for modulating an effector T cell-mediated immune response in a subject (e.g., human) in need thereof, the method involving administering to the subject an effective amount of an agent that modulates Helios expression or biological activity, thereby modulating the immune response. In one embodiment, the subject is identified as having a neoplasia or pathogen infection (e.g., chronic infection). In another embodiment, the subject is identified as having an autoimmune or inflammatory disease.

In another aspect, the invention provides a method for increasing an effector T cell-mediated immune response in a subject in need thereof, the method involving administering to the subject an effective amount of an agent that reduces Helios expression or biological activity, thereby increasing the immune response. In one embodiment, the subject has a neoplasia or pathogen infection.

In another aspect, the invention provides a method for treating neoplasia in a subject in need thereof, the method involving administering to the subject an effective amount of an agent that reduces Helios expression or biological activity, thereby treating the neoplasia. In one embodiment, the method reduces Treg suppression of an effector T cell mediated immune response. In another embodiment, the method further involves administering to the subject an immunogenic composition containing a tumor antigen. In yet another embodiment, the method enhances an immune response against a tumor antigen.

In yet another aspect, the invention provides a method for increasing the efficacy of an anti-neoplasia vaccine in a subject, the method involving administering to the subject a vaccine containing a tumor antigen and an agent that reduces the level or activity of a Helios polypeptide in a cell of the subject.

In still another aspect, the invention provides an inhibitory nucleic acid molecule that specifically binds a Helios polynucleotide sequence (e.g., human or rodent sequence). In one embodiment, the inhibitory nucleic acid molecule is a siRNA having the following polynucleotide sequence:

```
Sense:      CCUCACAAGUGCAACUACUtt    (SEQ ID NO: 1)

Antisense:  AGUAGUUGCACUUGUGAGGtt    (SEQ ID NO: 2)
```

In another embodiment, the inhibitory nucleic acid further comprises an aptamer that specifically binds to an immune cell. In still another embodiment, the immune cell is a regulatory T cell. In another embodiment, the aptamer binds neuropilin.

In another aspect, the invention provides an inhibitory nucleic acid molecule conjugated to an aptamer that specifically binds an immune cell (e.g., a regulatory T cell). In one embodiment, the aptamer binds neuropilin.

In another aspect, the invention provides a vector encoding the inhibitory nucleic acid molecule of any previous aspect.

In another aspect, the invention provides an expression vector containing a nucleic acid molecule encoding a Helios polypeptide. In one embodiment, the vector further comprises a promoter positioned for expression of Helios in a mammalian cell. In another embodiment, the vector is a lentivirus construct.

In another aspect, the invention provides a pharmaceutical composition for modulating an immune response, the composition containing an effective amount of an agent that reduces the expression or activity of a Helios polypeptide. In one embodiment, the siRNA is conjugated to an aptamer. In another embodiment, the aptamer binds an immune cell. In another embodiment, the polypeptide is an agent that specifically binds a Helios polypeptide and disrupts a Helios/FoxP3 interaction. In another embodiment, the subject is identified as having an autoimmune or inflammatory disease. In still another embodiment, the agent binds the FoxP3 promoter at about nucleotides −1184 to −724 and/or −692 to −335 from transcriptional start site and disrupts a Helios/FoxP3 interaction.

In another aspect, the invention provides a method for identifying an agent that modulates Treg suppressive activity, the method involving contacting a cell expressing a Helios nucleic acid molecule or polypeptide with a candidate agent; and detecting an alteration in the level of Helios polynucleotide or polypeptide in the contacted cell relative to the level in an untreated control cell, where an alteration in Helios expression identifies the agent as useful for modulating Treg suppressive activity. In one embodiment, the method identifies an agent that increases or decreases Helios transcription or translation. In another embodiment, the Helios polynucleotide level is detected using a polymerase chain reaction. In another embodiment, the Helios polypeptide level is detected in an immunoassay.

In another aspect, the invention provides a method for identifying a candidate compound that increases an effector T cell-mediated immune response, the method involving the steps of contacting a cell expressing a Helios polypeptide or polynucleotide with a candidate agent; and detecting a decrease in the level or biological activity of a Helios polypeptide or polynucleotide in the cell relative to an uncontacted control cell, where a decrease in the level or biological activity of the Helios polypeptide identifies the agent as useful for increasing the immune response. In one embodiment, Helios polypeptide expression is detected in an immunoassay. In another embodiment, Helios biological activity is monitored by detecting Helios binding to a FoxP3 promoter or FoxP3 expression. In another embodiment, Helios biological activity is monitored by detecting Treg suppressive activity.

In various embodiments of any of the above aspects, the following recitations apply. In one embodiment, the agent is a polypeptide, polynucleotide, or small compound. In embodiments of the above aspects, the polynucleotide is an inhibitory nucleic acid molecule that is any one or more of siRNA, shRNA, or antisense oligonucleotide. In other embodiments of the above aspects, the agent disrupts Helios binding to a FoxP3 promoter. In still other embodiments of the above aspects, the agent specifically binds a Helios polypeptide. In still other embodiments of the above aspects, the agent binds the FoxP3 promoter at about nucleotides −1184 to −724 and/or −692 to −335 from transcriptional start site. In still other embodiments, the method increases or reduces Treg suppressive activity. In embodiments of the above aspects, the polypeptide is an antibody that specifically binds a Helios polypeptide and disrupts a Helios/FoxP3 interaction. In other embodiments of the above aspects, the agent binds the FoxP3 promoter at about nucleotides −1184 to −724 and/or −692 to −335 from transcriptional start site and disrupts a Helios/FoxP3 interaction. In embodiments of the above aspects, the Helios inhibitory nucleic acid molecule is an siRNA having the following nucleic acid sequence:

```
Sense:      CCUCACAAGUGCAACUACUtt    (SEQ ID NO: 1)

Antisense:  AGUAGUUGCACUUGUGAGGtt    (SEQ ID NO: 2)
```

In other embodiments of any of the above aspects, the inhibitory nucleic acid further comprises an aptamer that specifically binds to an immune cell (e.g., a regulatory T cell). In another embodiment, the aptamer binds neuropilin.

The invention provides methods for enhancing a desirable immune response, such as an immune response against a tumor associated antigen, pathogen infection, or chronic infection, or for reducing an undesirable immune response, such as an immune response associated with an autoimmune or inflammatory disease. Compositions and articles defined by the invention were isolated or otherwise manufactured in connection with the examples provided below. Other features and advantages of the invention will be apparent from the detailed description, and from the claims.

Definitions

By "Helios polypeptide" is meant a zinc finger DNA binding protein or fragment thereof that is substantially identical to the amino acid sequence provided at NCBI Accession No. AAF09441 and that has Helios biological activity. An exemplary sequence of a Helios polypeptide is provided at FIG. 3A and below:

```
                                                            (SEQ ID NO: 3)
  1 metdaidgyi tcdnelsper ehsnmaidlt sstpngqhas pshmtstnsv klemqsdeec 61 drkplsrene irghdegssl eepliessev adnrkvqelq geggirlpng klkcdvcgmv 121 cigpnvlmvh krshtgerpf hcnqcgasft qkgnllrhik lhsgekpfke pfcsyacrrr
```

-continued

```
181 daltghlrth svgkphkcny cgrsykqrss leehkerchn ylqnvsmeaa gqvmshhvpp 241 medckeqepi mdnnislvpf erpavieklt gnmgkrksst pqkfvgeklm rfsypdihfd 301 mnltyekeae lmqshmmdqa innaitylga ealhplmqhp pstiaevapv issaysqvyh 361 pnrierpisr etadshennm dgpislirpk srpqereasp snscldstds esshddhqsy 421 qghpalnpkr kqspaymked vkaldttkap kgslkdiykv fngegeqira fkcehcrvlf 481 ldhvmytihm gchgyrdple cnicgyrsqd ryefsshivr gehtfh.
```

By "Helios nucleic acid molecule" is meant a polynucleotide encoding a Helios polypeptide.

By "Helios biological activity" is meant transcriptional regulatory activity, DNA binding activity, or modulation of an immune response.

By "FoxP3 promoter" is meant a polynucleotide sequence upstream of the FoxP3 polypeptide transcription start site that is sufficient to drive FoxP3 expression. A sequence for the FoxP3 promoter is provided at NCBI Accession No. AF235097 (FIG. 3B). In particular, a FoxP3 promoter comprises at least about −1184 to −335 from the transcriptional start site. An exemplary FoxP3 polynucleotide sequence is provided at NCBI Accession No. NM_14009, which is reproduced below:

(SEQ ID NO: 4)
```
   1 gcacacactc atcgaaaaaa atttggatta ttagaagaga gaggtctgcg gcttccacac 61 cgtacagcgt ggtttttctt ctcggtataa aagcaaagtt gattttgata cgtgacagtt 121 tcccacaagc caggctgatc cattttcgtc agtccacttc accaagcctg cccttggaca 181 aggacccgat gcccaaccccc aggcctggca agcccctcggc cccttccttg gcccttggcc 241 catccccagg agcctcgccc agctggaggg ctgcacccaa agcctcagac ctgctggggg 301 cccggggccc aggggggaacc ttccagggcc gagatcttcg aggcggggcc catgcctcct 361 cttcttcctt gaacccccatg ccaccatcgc agctgcagct gcccacactg ccccctagtca 421 tggtggcacc ctccggggca cggctgggcc ccttgcccca cttacaggca ctcctccagg 481 acaggccaca tttcatgcac cagctctcaa cggtggatgc ccacgcccgg acccctgtgc 541 tgcaggtgca cccccctggag agcccagcca tgatcagcct cacaccaccc accaccgcca 601 ctggggtctt ctccctcaag gcccggcctg gcctcccacc tgggatcaac gtggccagcc 661 tggaatgggt gtccaggag ccggcactgc tctgcaccct cccaaatccc agtgcaccca 721 ggaaggacag caccctttcg gctgtgcccc agagctccta cccactgctg gcaaatggtg 781 tctgcaagtg gcccggatgt gagaaggtct tcgaagagcc agaggacttc ctcaagcact 841 gccaggcgga ccatcttctg gatgagaagg gcagggcaca atgtctcctc cagagagaga 901 tggtacagtc tctggagcag cagctggtgc tggagaagga gaagctgagt gccatgcagg 961 cccacctggc tgggaaaatg gcactgacca aggcttcatc tgtggcatca tccgacaagg 1021 gctcctgctg catcgtagct gctggcagcc aaggccctgt cgtcccagcc tggtctggcc 1081 cccggggaggc ccctgacagc ctgtttgctg tccggaggca cctgtggggt agccatggaa 1141 acagcacatt cccagagttc ctccacaaca tggactactt caagttccac aacatgcgac 1201 cccctttcac ctacgccacg ctcatccgct gggccatcct ggaggctcca gagaagcagc 1261 ggacactcaa tgagatctac cactggttca cacgcatgtt tgccttcttc agaaaccatc 1321 ctgccacctg gaagaacgcc atccgccaca acctgagtct gcacaagtgc tttgtgcggg 1381 tggagagcga gaaggggggct gtgtggaccg tggatgagct ggagttccgc aagaaacgga 1441 gccagaggcc cagcaggtgt tccaacccta cacctggccc ctgacctcaa gatcaaggaa 1501 aggaggatgg acgaacaggg gccaaactgg tgggaggcag aggtggtggg ggcagggatg 1561 ataggccctg gatgtgccca cagggaccaa gaagtgaggt ttccactgtc ttgcctgcca 1621 gggcccctgt tccccgctg gcagccaccc cctcccccat catatccttt gccccaaggc
```

```
-continued
1681 tgctcagagg ggccccggtc ctggcccag ccccacctc cgccccagac acaccccca 1741 gtcgagccct gcagccaaac agagccttca caaccagcca cacagagcct gcctcagctg 1801 ctcgcacaga ttacttcagg gctggaaaag tcacacagac acacaaaatg tcacaatcct 1861 gtccctcact caacacaaac cccaaaacac agagagcctg cctcagtaca ctcaaacaac 1921 ctcaaagctg catcatcaca caatcacaca caagcacagc cctgacaacc cacacacccc 1981 aaggcacgca cccacagcca gcctcagggc ccacaggggc actgtcaaca caggggtgtg 2041 cccagaggcc tacacagaag cagcgtcagt accctcagga tctgaggtcc caacacgtgc 2101 tcgctcacac acacggcctg ttagaattca cctgtgtatc tcacgcatat gcacacgcac 2161 agcccccag tgggtctctt gagtcccgtg cagacacaca cagccacaca cactgccttg 2221 ccaaaaatac cccgtgtctc ccctgccact cacctcactc ccattccctg agccctgatc 2281 catgcctcag cttagactgc agaggaacta ctcatttatt tgggatccaa ggcccccaac 2341 ccacagtacc gtccccaata aactgcagcc gagctcccca caaaaaaaaa aaaaaaa
```

By "effector T cell" is meant a lymphocyte that secretes cytokines and functions in an adaptive immune response. Such cells include CD4 T cells that play a role in the induction, maintenance and maturation of an antibody response, as well as CD8 T cells which can directly kill both tumor cells and cells infected with a virus.

By "effector T cell-mediated immune response" is meant any immune response mediated by an effector T cell.

By "Treg" or "regulatory T cell" is meant a CD4+CD25+ T cells that suppresses CD4+CD25− T cell proliferation and/or effector function, or that otherwise down-modulates an immune response. Notably, Treg may down-regulate immune responses mediated by Natural Killer cells, Natural Killer T cells as well as other immune cells.

By "regulatory T cell suppressive activity" is meant any biological function of a Treg that results in a reduction in CD4$^+$CD25$^−$ T cell proliferation or a reduction in an immune response. In particular embodiments, regulatory T cell suppressive activity reduces an effector T cell-mediated immune response.

By "regulatory T cell biological function" is meant regulatory T cell modulation of an immune response.

By "neuropilin polypeptide" is meant a protein having substantial identity to NCBI Accession No. AAC51759. Neuropilin (NRP1) is a membrane-bound coreceptor to a tyrosine kinase receptor for both vascular endothelial growth factor and semaphorin family members. NRP1 plays versatile roles in angiogenesis, axon guidance, cell survival, migration, and invasion. It is also expressed on Tregs. Thus, aptamers and antibodies that bind neuropilin or another polypeptide expressed on Tregs may be used to target an agent of the invention (e.g. siRNA).

An exemplary neuropilin amino acid sequence is provided below:

```
                                                          (SEQ ID NO: 5)
   1 merglpllca vlalvlapag afrndevgdt ikiespgylt spgyphsyhp sekcewliqa 61 pdpygrimin fnphfdledr dekydyvevf dgenenghfr gkfcgkiapp pvvssgpflf 121 ikfvsdyeth gagfsiryei fkrgpecsqn yttpsgviks pgfpekypns lectyivfap 181 kmseiilefe sfdlepdsnp pggmfcrydr leiwdgfpdv gphigrycgq ktpgrirsss 241 gilsmvfytd saiakegfsa nysvlqssvs edfkcmealg mesgeihsdq itassqystn 301 wsaersrlny pengwtpged syrewiqvdl gllrfvtavg tqgaisketk kkyyvktyki 361 dvssngedwi tikegnkpvl fqgntnptdv vvavfpkpli trfvrikpat wetgismrfe 421 vygckitdyp csgmlgmvsg lisdsqitss nqgdrnwmpe nirlvtsrsg walppaphsy 481 inewlqidlg eekivrgiii qggkhrenkv fmrkfkigys nngsdwkmim ddskrkaksf 541 egnnnydtpe lrtfpalstr firiyperat hgglglrmel lgceveapta gpttpngnlv 601 decdddqanc hsgtgddfql tggttvlate kptvidstiq sefptygfnc efgwgshktf 661 chwehdnhvq lkwsvltskt gpiqdhtgdg nfiysqaden qkgkvarlvs pvvysqnsah 721 cmtfwyhmsg shvgtlrvkl ryqkpeeydq lvwmaighqg dhwkegrvll hkslklyqvi 781 fegeigkgnl ggiavddisi nnhisqedca kpadldkknp eikidetgst pgyegegegd 841 knisrkpgnv lktlepilit iiamsalgvl lgavcgvvly cacwhngmse rnlsalenyn 901 felvdgvklk kdklntqsty sea
```

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the object to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of agents for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "immunological assay" is meant an assay that relies on an immunological reaction, for example, antibody binding to an antigen. Examples of immunological assays include ELISAs, Western blots, immunoprecipitations, and other assays known to the skilled artisan.

By "inflammation" is meant any excessive or undesirable immune response associated with tissue damage.

By "inflammatory disease" is meant a pathology associated with an undesirable immune response.

By "inhibitory nucleic acid molecule" is meant a single or double-stranded polynucleotide that reduces the expression of a target gene or polypeptide. Exemplary inhibitory nucleic acid molecules include siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, inhibitory nucleic acid molecule comprises or is complementary to at least a portion of a target nucleic acid molecule, or an ortholog thereof described herein.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "modulation" is meant a positive or negative alteration.

By "neoplasia" or "neoplasm" is meant a disease characterized by the pathological proliferation of a cell or tissue and its subsequent migration to or invasion of other tissues or organs.

By "nucleic acid molecule" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

As used herein, "obtaining" as in "obtaining an agent" includes synthesizing, purchasing, or otherwise acquiring the agent.

By "pathogen" is meant any bacteria, viruses, fungi, or parasite capable of interfering with the normal function of a cell.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "promoter" is meant a polynucleotide sufficient to direct transcription.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant an agent or antibody that recognizes and binds a polypeptide or polynucleotide of the invention, but which does not substantially recognize and bind other molecules in a sample, for example, a biological sample, which naturally includes a polypeptide or polynucleotide of the invention.

By "subject" is meant a mammal, including, but not limited to, a human or non-human mammal, such as a bovine, equine, canine, ovine, or feline.

By "substantially identical" is meant a polypeptide or nucleic acid molecule exhibiting at least 85% identity to a reference amino acid sequence or nucleic acid sequence. Preferably, such a sequence is at least 85%, 90%, 95% or even 99% identical at the amino acid level or nucleic acid to the sequence used for comparison.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1%

SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

BRIEF DESCRIPTION OF THE DRAWINGS

FIG. 1A is a graph that quantitates relative message levels of Helios and FoxP3 in CD4$^+$ CD25$^-$ and CD4$^+$ CD25$^+$. This experiment was repeated three times. FIG. 1B is a graph showing the relative timing of Helios and FoxP3 expression in CD4$^+$ CD25$^-$ T cells post-activation with immobilized 0.5 µg/mL anti-CD3e and soluble 1 ug/mL of anti-CD28. FIG. 1C shows results of a FACS analysis of a time course of Helios induced apoptosis in Jurkat T cells transfected with the indicated constructs. The term "7AAD" denotes 7-Aminoactinomycin. The term "AnnxV" denotes annexin-V. FIG. 1D provides schematic diagram, which shows the portions of the FoxP3 promoter that were immunoprecipitated, and four Western blots showing results of the ChiP assay. ChiP assays were performed using EL4 cells transfected with Myc tagged Helios or an insert control and FoxP3 promoter primers shown.

FIG. 2A is a graph showing the relative message levels of Helios in CD4$^+$CD25$^-$ and CD4$^+$CD25$^+$ expressing T cells. FIG. 2B is a graph showing relative message levels of FoxP3 in CD4$^+$CD25$^-$ and CD4$^+$CD25$^+$. FIGS. 2C and 2D are graphs showing the results of Treg assays. Responder CD4$^+$CD25$^-$ T cells were admixed with untransfected or siRNA transfected suppressor CD4$^+$CD25$^+$ T cells in a 1:1 ratio. Proliferation of responders was assayed by H$^3$-thymidine incorporation (FIG. 2C) or Carboxyfluorescein succinimidyl ester (CFSE) dilution. FIG. 2D shows CFSE results after 5 days of activation. Suppression assay was repeated four times using three individual donors.

FIGS. 3A and 3B provide the amino acid sequence of the Helios protein showing the DNA binding domains with underlining and the nucleic acid sequence of the human FoxP3 promoter. The sequence corresponding to the mouse Helios Chip target is underlined.

DETAILED DESCRIPTION OF THE INVENTION

Figures 1A, 1B, 1C, 1D:
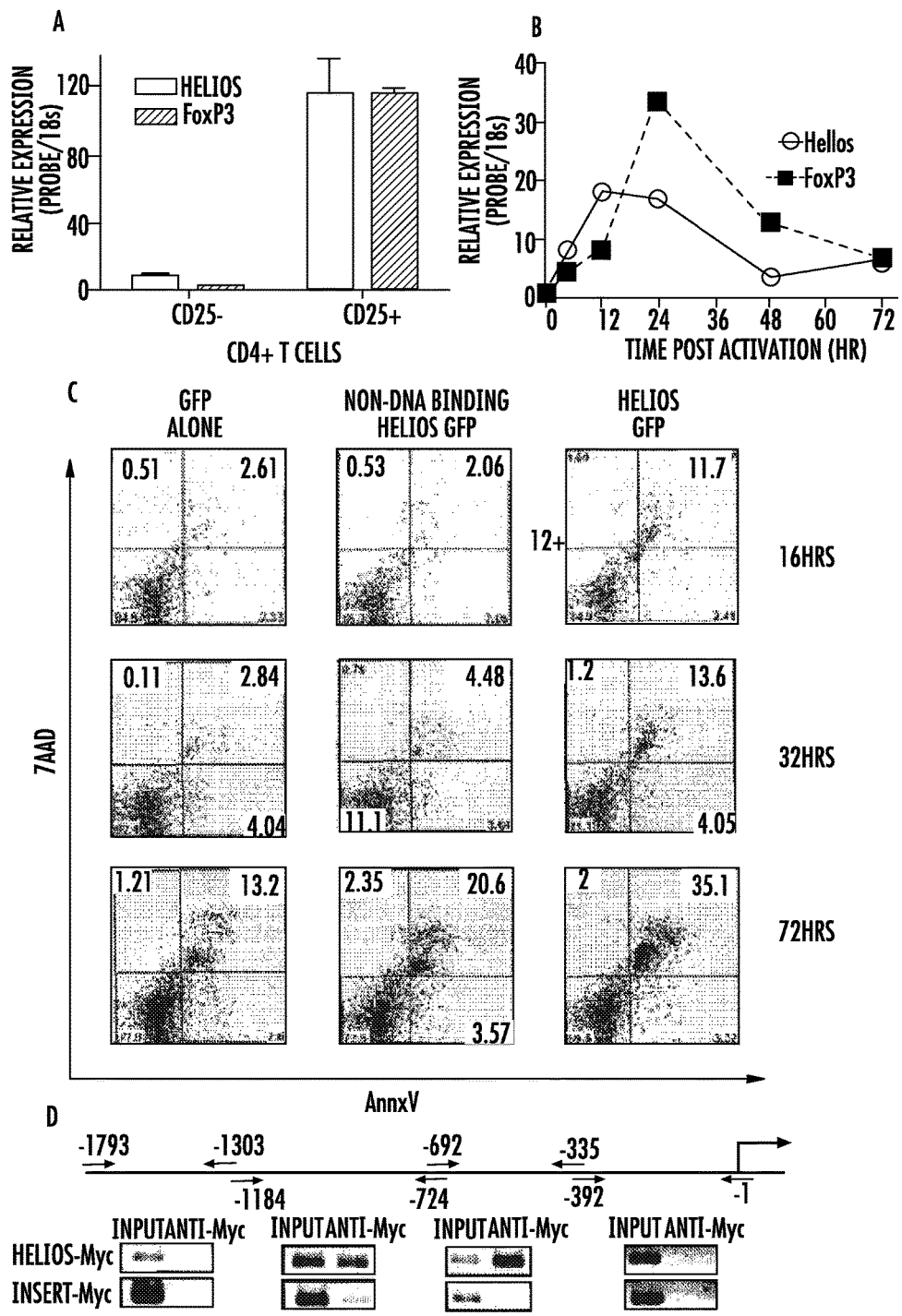
FIGS. 1A-1D show Helios and FoxP3 expression analysis.

The invention features compositions and methods that are useful for modulating regulatory T cell suppressive activity. The invention is based, at least in part, on the discovery that the transcription factor Helios binds to at least two sites on the FoxP3 promoter, and that suppression of Helios message in CD4$^+$CD25$^+$ T cells attenuates FoxP3 levels and significantly attenuated the immunosuppressive function of the regulatory T cells.

Regulatory T Cells

T cells are lymphocytes that play an important role in cell mediated immunity. A subset of CD4$^+$ T cells known as regulatory T cells act as a brake on the immune response by inhibiting effector T cells. By dampening the immune system's activity, regulatory T cells beneficially limit tissue damage and inflammation associated with innate and adoptive immune responses. Regulatory T cells are also important in maintaining immune tolerance to limit autoimmunity and in regulating homeostatic lymphocyte expansion. However, they also suppress natural immune responses to parasites and viruses, as well as antitumor immunity induced by therapeutic vaccines. The development and function of regulatory T cells depend on the expression of the transcription factor forkhead box P3 (FOXP3).

As reported in more detail below, the Ikaros family transcription factor Helios is up-regulated in natural regulatory T cells (Treg), but no role for Helios in Treg function has yet been described. After first confirming that Helios is upregulated in human CD4$^+$CD25$^+$ Treg, Chromatin ImmunoPrecipitation (ChIP) experiments were performed which showed that Helios binds to the FoxP3 promoter. Specifically, Helios binds two separate but adjacent regions (−1184 to −724 and −692 to −335 from transcriptional start site) on the FoxP3 promoter and regulates FoxP3 transcription in T cells. Helios knockdown resulted in a decrease in levels of FoxP3 message and a decrease in Treg suppressive activity. Functionally, these data were supported by experiments showing that knocking down Helios with siRNA resulted in the down-regulation of FoxP3. Interestingly, suppression of Helios message in CD4$^+$CD25$^+$ T cells significantly attenuated their suppressive function. Taken together, these data indicate that Helios plays an important role in regulatory T cell function and indicates that Helios is a novel target to manipulate Treg activity in a clinical setting. Accordingly, the invention provides therapeutic and prophylactic compositions and methods for modulating Treg activity. Agents that reduce Helios expression or biological activity also reduce the suppressive activity of regulatory T cells.

Agents that reduce Helios expression or biological activity release the Treg brake on the immune response (e.g., an effector T cell-mediated immune response). Such agents are useful for enhancing an immune response in a subject in need thereof. In particular, such agents are useful for the treatment of neoplasia, alone or in combination with therapeutics that induce antitumor immunity, such as anti-cancer vaccines.

In other embodiments, the present invention provides agents that increase Helios expression or activity, thereby increasing Treg suppressive activity and reducing immune responsiveness. Such agents are useful for the treatment of diseases associated with an undesirable immune response (e.g., reducing autoimmunity, reducing inflammation associated tissue damage). The invention provides for the identification of agents that modulate an immune response (e.g., an immune response mediated by effector T cells), including antibodies, peptides, peptide mimetics, aptamers, and polynucleotides.

RNA Interference Therapy

The invention features the novel and therapeutically important discovery that the use of RNA interference (RNAi) to reduce Helios expression also reduces regulatory T cell suppressive activity. Accordingly, agents that reduce helios expression or biological activity render neoplastic cells more susceptible to anti-cancer vaccines and other chemotherapeutics that enhance an anti-neoplasia immune response. The methods of the invention provide inhibitory nucleic acid molecules (e.g., siRNA, shRNA, and antisense polynucleotides) that are useful for reducing regulatory T cell suppressive activity. In one embodiment, the invention provides nucleobase oligomers that are employed in double-stranded RNAs for RNAi-mediated knockdown of Helios expression. If desired, siRNAs or other inhibitory nucleic acid molecules are targeted to specific cells. In one approach, such targeting is accomplished by conjugating the inhibitory nucleic acid molecule (e.g., anti-helios siRNA) to a cell-surface specific aptamer targeted at CD4 or CD24-expressing cell, for example. Such methods are known in the art and described, for example, by Chu et al., "Aptamer mediated siRNA delivery," Nucleic Acids Research, 2006, Vol. 34, No. 10 e73. Methods for targeting siRNAs are described, for example in International Patent Application No. WO2009046104 entitled "APTAMER-TARGETED SIRNA TO PREVENT ATTENUATION OR SUPPRESSION OF T CELL FUNCTION" was published on Apr. 9, 2009. In another approach, a monoclonal antibody is used to target an inhibitory nucleic acid molecule (e.g., anti-helios siRNA) to the cell.

RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). In RNAi, gene silencing is typically triggered post-transcriptionally by the presence of double-stranded RNA (dsRNA) in a cell. This dsRNA is processed intracellularly into shorter pieces called small interfering RNAs (siRNAs). The introduction of siRNAs into cells either by transfection of dsRNAs or through expression of siRNAs using a plasmid-based expression system is increasingly being used to create loss-of-function phenotypes in mammalian cells.

In one embodiment of the invention, a double-stranded RNA (dsRNA) molecule is made. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs consist of a stem-loop structure with optional 3' UU-overhangs. While there may be variation, stems can range from twenty-one to thirty-one base pairs (desirably twenty-five to twenty-nine base pairs), and the loops can range from four to thirty base pairs (desirably four to twenty-three base pairs). For expression of shRNAs within cells, plasmid vectors containing, e.g., the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Computer programs that employ rational design of oligos are useful in predicting regions of the helios sequence that may be targeted by RNAi. For example, see Reynolds et al, Nat. Biotechnol., 22:326-330, 2004, for a description of the Dharmacon siDESIGN tool.

Ribozymes

Catalytic RNA molecules or ribozymes that include an antisense helios sequence of the present invention can be used to inhibit expression of a helios nucleic acid molecule in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference. Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Antisense Therapy

In another embodiment, helios antisense nucleic acids may be employed in the methods of the invention. The technique is based on the principle that sequence-specific suppression of gene expression can be achieved by intracellular hybridization between mRNA and a complementary antisense species. The formation of a hybrid RNA duplex may then interfere with the processing/transport/translation and/or stability of the target helios mRNA. Antisense strategies may use a variety of approaches, including the use of antisense oligonucleotides and injection of antisense RNA. An exemplary approach features transfection of antisense RNA expression vectors into targeted cells. Antisense effects can be induced by control (sense) sequences; however, the extent of phenotypic changes are highly variable. Phenotypic effects induced by antisense effects are based on changes in criteria such as protein levels, protein activity measurement, and target mRNA levels.

Computer programs such as OLIGO (previously distributed by National Biosciences Inc.) may be used to select candidate nucleobase oligomers for antisense therapy based on the following criteria: 1) no more than 75% GC content, and no more than 75% AT content; 2) preferably no nucleobase oligomers with four or more consecutive G residues; 3) no nucleobase oligomers with the ability to form stable dimers or hairpin structures; and 4) sequences around the translation start site are a preferred region. In addition, accessible regions of the target mRNA may be predicted with the help of the RNA secondary structure folding program MFOLD (M. Zuker, D. H. Mathews & D. H. Turner, Algorithms and Thermodynamics for RNA Secondary Structure Prediction: A Practical Guide. In: RNA Biochemistry and Biotechnology, J. Barciszewski & B. F. C. Clark, eds., NATO ASI Series, Kluwer Academic Publishers, (1999). Polynucleotides that only partially fulfill some of the above selection criteria may also be chosen as possible candidates if they recognize a predicted open region of the target mRNA.

Delivery of Nucleobase Oligomers

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Targeted Agent Delivery

If desired, an inhibitory nucleic acid molecule, such as a small interfering RNA (siRNA), is delivered to a specific cell-type using an aptamer. For example, agents described herein are targeted to cells of the immune system, such as, for example, immune effector cells, cells involved in the regulation of the immune system, e.g. T regulatory cells (Treg), antigen presenting cells and the like. Examples of antigen presenting cells include, dendritic cells, b cells, monocytes/macrophages. Aptamers are oligonucleotide-based ligands that exhibit specificity and avidity comparable or superior to antibodies. Unlike antibodies, aptamers are chemically synthesized. Many different permutations and combinations of aptamers and inhibitory nucleic acid molecules can be used. For example, an siRNA can be attached to one or more aptamers or encoded as a single molecule so that the 5' to 3' would encode for an aptamer, the siRNA and an aptamer. The aptamers and inhibitory nucleic acid molecules can also be attached via linker molecules. The composition can also comprise in a 5' to 3' direction an aptamer attached to another aptamer via a linker. The aptamers are then attached to the siRNA. These molecules can also be encoded in a desired combination.

In certain embodiments, the nucleic acid molecules of the present disclosure can be synthesized separately and joined together post-synthetically, for example, by ligation (Moore et al, Science 256:9923, 1992; Draper et al., PCT Publication No. WO 93/23569; Shabarova et al, Nucleic Acids Res. 19:4241, 1991; Bellon et al., Nucleosides & Nucleotides 16:951, 1997; Bellon et al., Bioconjugate Chem. 5:204, 1997), or by hybridization following synthesis or deprotection. In further embodiments, RNAi's can be made as single or multiple transcription products expressed by a polynucleotide vector encoding one or more siRNAs and directing their expression within host cells. An inhibitory nucleic acid molecule or analog thereof described herein may comprise a nucleoside, non-nucleotide, or mixed nucleotide/non-nucleotide linker that joins the aptamers and RNAi's. In one embodiment, a nucleotide linker can be a linker of more than about 2 nucleotides length up to about 50 nucleotides in length. In another embodiment, the nucleotide linker can be a nucleic acid aptamer.

By "aptamer" or "nucleic acid aptamer" as used herein is meant a nucleic acid molecule that binds specifically to a target molecule wherein the nucleic acid molecule has a sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al, Annu. Rev. Biochem. 64:163, 1995; Brody and Gold, J. Biotechnol. 74:5, 2000; Sun, Curr. Opin. Mol. Ther. 2:100, 2000; Kusser, J. Biotechnol. 74:21, 2000; Hermann and Patel, Science 257:820, 2000; and Jayasena, Clinical Chem. 45:1628, 1999).

A non-nucleotide linker may be comprised of an abasic nucleotide, polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, Nucleic Acids Res. 18:6353, 1990, and Nucleic Acids Res. 15:3113, 1987; Cload and Schepartz, J. Am. Chem. Soc. 113:6324, 1991; Richardson and Schepartz, J. Am Chem Soc. 113:5109, 1991; Ma et al., Nucleic Acids Res 21:2585, 1993, and Biochemistry 32: 1751, 1993; Durand et al., Nucleic Acids Res. 18:6353, 1990; McCurdy et al., Nucleosides & Nucleotides 10:281, 1991; Jaschke et al., Tetrahedron Lett. 34:301, 1993, Ono et al, Biochemistry 50:9914, 1991; Arnold et al, PCT Publication No. WO 89/02439; Usman et al, PCT Publication No. WO 95/06731; Dudycz et al, PCT Publication No. WO 95/11910 and Ferentz and Verdine, J. Am. Chem. Soc. 113:4000, 1991.

The invention may be used against protein coding gene products as well as non-protein coding gene products. Examples of non-protein coding gene products include gene products that encode ribosomal RNAs, transfer RNAs, small nuclear RNAs, small cytoplasmic RNAs, telomerase RNA, RNA molecules involved in DNA replication, chromosomal rearrangement and the like. In accordance with the invention, siRNA oligonucleotide therapies comprise administered siRNA oligonucleotide which contacts (interacts with) the targeted mRNA from the gene, whereby expression of the gene is modulated. Such modulation of expression suitably can be a difference of at least about 10% or 20° % relative to a control, more preferably at least about 30%, 40%. 50° %, 60%, 70%0, 80%, or 90%0 difference in expression relative to a control.

Generation of Aptamers

Aptamers are high affinity single-stranded nucleic acid ligands which can be isolated from combinatorial libraries through an iterative process of in vitro selection known as SELEX™ (Systemic Evolution of Ligands by Exponential enrichment) Aptamers exhibit specificity and avidity comparable to or exceeding that of antibodies, and can be generated against most targets. In one embodiment, an siRNA is linked to at least one aptamer which is specific for a desired cell and target molecule. In other embodiments, the RNAi's are combined with two aptamers.

Aptamers specific for a given biomolecule can be identified using techniques known in the art. See, e.g., Toole et al. (1992) PCT Publication No. WO 92/14843; Tuerk and Gold (1991) PCT Publication No. WO 91/19813; Weintraub and Hutchinson (1992) PCT Publication No 92/05285; and Ellington and Szostak, Nature 346:818 (1990). Briefly, these techniques typically involve the complexation of the molecular target with a random mixture of oligonucleotides. The aptamer-molecular target complex is separated from the uncomplexed oligonucleotides. The aptamer is recovered from the separated complex and amplified. This cycle is repeated to identify those aptamer sequences with the highest affinity for the molecular target.

The SELEX™ process is a method for the in vitro evolution of nucleic acid molecules with highly specific binding to target molecules and is described in, e.g., U.S. Pat. No. 5,270,163 (see also WO 91/19813) entitled "Nucleic Acid Ligands". Each SELEX-identified nucleic acid ligand is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

SELEX™ relies as a starting point upon a large library of single stranded oligonucleotides comprising randomized sequences derived from chemical synthesis on a standard DNA synthesizer. The oligonucleotides can be modified or unmodified DNA, RNA or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a pre-selected purpose such as, CpG motifs, hybridization sites for PCR primers, promoter sequences for RNA polymerases (e.g., T3, T4. T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs See, e.g., U.S. Pat. Nos. 5,958,691; 5,660,985; 5,958,691; 5,698,687; 5,817, 635; 5,672,695, and PCT Publication WO 92/07065. Random oligonucleotides can be synthesized from phosphodiester-linked nucleotides using solid phase oligonucleotide synthesis techniques well known in the art. See, e.g., Froehler et al, Nucl. Acid Res. 14:5399-5467 (1986) and Froehler et al, Tet. Lett. 27:5575-5578 (1986). Random oligonucleotides can also be synthesized using solution phase methods such as triester synthesis methods. See, e.g., Sood et al, Nucl. Acid Res. 4:2557 (1977) and Hirose et al, Tet. Lett., 28:2449 (1978). Typical syntheses carried out on automated DNA synthesis equipment yield $10^{14}$-$10^{16}$ individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be either RNA or DNA. In those instances where an RNA library is to be used as the starting library it is typically generated by transcribing a DNA library in vitro using T7 RNA polymerase or modified T7 RNA polymerases and purified. The RNA or DNA library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process. In one embodiment of SELEX™, the selection process is so efficient at isolating those nucleic acid ligands that bind most strongly to the selected target, that only one cycle of selection and amplification is required Such an efficient selection may occur, for example, in a chromato graphic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides and in some embodiments, about 30 to about 40 nucleotides. In one example, the 5'-fixed:random:3'-fixed sequence comprises a random sequence of about 30 to about 50 nucleotides.

The core SELEX™ method can be modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photo reactive groups capable of binding and/or photo-cross linking to and/or photo-inactivating a target molecule. U.S. Pat. Nos. 5,567,588 and 5,861,254 describe SELEX™ based methods which achieve highly efficient partitioning between oligonucleotides having high and low affinity for a target molecule U.S. Pat. No. 5,496,938 describes methods for obtaining improved nucleic acid ligands after the SELEX™ process has been performed. U.S. Pat. No. 5,705,337 describes methods for covalently linking a ligand to its target. SELEX™ can also be used to obtain nucleic acid ligands that bind to more than one site on the target molecule, and to obtain nucleic acid ligands that include non-nucleic acid species that bind to specific sites on the target.

The SELEX™ method encompasses the identification of high-affinity nucleic acid ligands containing modified nucleotides conferring improved in vivo stability or improved delivery characteristics. Examples of such modifications include chemical substitutions at the ribose and/or phosphate and/or base positions. For example, oligonucleotides containing nucleotide derivatives chemically modified at the 2' position of ribose, 5 position of pyrimidines, and 8 position of purines, 2'-modified pyrimidines, nucleotides modified with 2'-amino (2'-$NH_2$), 'T-fluoro (2'-F), and/or 2'-O-methyl (2'-OMe) substituents.

Pre-SELEX™ process modifications or those made by incorporation into the SELEX™ process yield nucleic acid ligands with both specificity for their SELEX™ target and improved stability, e.g., in vivo stability. Post-SELEX™ process modifications made to nucleic acid ligands may result in improved stability. e.g., in vivo stability without adversely affecting the binding capacity of the nucleic acid ligand.

The SELEX™ method encompasses combining selected oligonucleotides with other selected oligonucleotides and non-oligonucleotide functional units as described in U.S. Pat. Nos. 5,637,459 and 5,683,867. The SELEX™ method further encompasses combining selected nucleic acid ligands with lipophilic or non-immunogenic high molecular weight compounds in a diagnostic or therapeutic complex, as described, e.g., in U.S. Pat. Nos. 6,011,020, 6,051,698, and PCT Publication No. WO 98/18480. These patents and applications teach the combination of a broad array of shapes and other properties, with the efficient amplification and replication properties of oligonucleotides, and with the desirable properties of other molecules. The identification of nucleic acid ligands to small, flexible peptides via the SELEX™ method can also be used in embodiments of the invention. Small peptides have flexible structures and usually exist in solution in an equilibrium of multiple conformers.

The aptamers with specificity and binding affinity to the target(s) of the present invention are typically selected by the SELEX™ process as described herein. As part of the SELEX™, process, the sequences selected to bind to the target can then optionally be minimized to determine the minimal sequence having the desired binding affinity. The selected sequences and/or the minimized sequences are optionally optimized by performing random or directed mutagenesis of the sequence to increase binding affinity or alternatively to determine which positions in the sequence are essential for binding activity. Additionally, selections can be performed with sequences incorporating modified nucleotides to stabilize the aptamer molecules against degradation in vivo.

The results show that the aptamer-RNAi compositions enter cells and sub-cellular compartments. However, further aptamers can be obtained using various methods. In a preferred embodiment, a variation of the SELEX™ process is used to discover aptamers that are able to enter cells or the sub-cellular compartments within cells. These delivery aptamers will allow or increase the propensity of an oligonucleotide to enter or be taken up by a cell.

Therapeutic Agents of the Invention

Any agent that modulates an activity of Helios is likely to be useful in the methods of the invention. As reported herein, Helios binds to the FoxP3 promoter and regulates FoxP3 transcription. Formation of a helios polypeptide/FoxP3 promoter complex indicates that agents that disrupt a Helios/FoxP3 interaction (e.g., small compounds, polynucleotides, polypeptides, such as antibodies, peptides, peptide derivatives, aptamers) are useful for modulating an immune response (e.g., an immune response mediated by effector T cells). In one embodiment, the invention provides agents that specifically bind to a Helios polypeptide or FoxP3 promoter and reduce a Helios/FoxP3 interaction. For example, the invention provides agents that specifically bind to Helios polypeptide and disrupt binding to the FoxP3 promoter. In other embodiments, an agent of the invention binds at or near the Helios binding site on the FoxP3 promoter (e.g., −1184 to −724 and −692 to −335 from transcriptional start site on the FoxP3 promoter), thereby reducing or preventing Helios binding to the promoter.

Agents that increase Treg suppressive activity are useful for reducing an undesirable immune response for the treatment of autoimmune or inflammatory disease. Autoimmune disorders arise when the body produces an inappropriate immune response against its own tissues. This is typically associated with the production of autoantibodies, which cause inflammation and tissue damage. Autoimmune and inflammatory diseases include, but are not limited to, asthma, allergy, allergic airway inflammation, inflammatory bowel disease, arthritis, rheumatoid arthritis and Juvenile rheumatoid arthritis, Type 1 Diabetes Mellitus, Lupus, Systemic Lupus Erythematosus, Hashimoto's thyroiditis, Graves' disease, Scleroderma, Celiac disease, Crohn's disease, Ulcerative colitis, Sjogren's syndrome, Goodpasture's syndrome, Addison's disease, Wegener's granulomatosis, Primary biliary cirrhosis, Sclerosing cholangitis, Autoimmune hepatitis, Polymyalgia Rheumatica, systemic lupus erythematosus, Bechet's disease, Guillain-Barre syndrome, and various vasculitides.

Agents that reduce Treg suppressive activity are useful for enhancing a desirable immune response for the treatment of neoplasia, for the treatment of chronic infections, or for the treatment of pathogen infections. In particular embodiments, the invention provides for the treatment of parasite infections, where Treg activity suppresses a host immune response.

Treatment of Pathogen Infections

Regulatory T cells suppress natural immune responses to parasites and viruses. The invention provides methods for enhancing an immune response for the treatment of pathogen infections, which include parasite infections, viral infections, and chronic infections (e.g., chronic bacterial infections). Parasites are organisms which depend upon other organisms in order to survive and thus must enter, or infect, another organism to continue their life cycle. The infected organism, i.e., the host, provides both nutrition and habitat to the parasite. Parasites can be classified based on whether they are intracellular or extracellular. An "intracellular parasite" as used herein is a parasite whose entire life cycle is intracellular. The invention provides methods for the treatment of intracellular and extracellular parasites. Human parasites include *Leishmania* (*Leishmania braziliensis*, *Leishmania donovani*, *Leishmania tropica*), *Plasmodium*, *Babesia* (e.g., *Babesia microti*, *Babesia divergens*), *Trichinella spiralis*, *Entamoeba histolytica*, *Giardia lamblia*, *Enterocytozoon bieneusi*, *Naegleria*, *Acanthamoeba*, *Isospora*, *Cryptosporidium*, *Eimeria*, *Neospora*, *Sarcocystis*, and *Schistosoma*, *Trypanosoma gambiense*, *Trypanosoma rhodesiense* (African sleeping sickness), *Trypanosoma cruzi* (Chagas' disease), and *Toxoplasma gondii*.

Fungi cause invasive diseases in hosts with reduced immunity, such as patients with HIV infection, organ or bone marrow transplants, or neutropenia following cancer immunotherapy. One of the most troublesome pathogenic fungi is *Candida*. There are approximately 200 species of the genus *Candida*, but nine cause the great majority of human infections. They are *C. albicans*, *C. krusei*, *C. glabrata* (formerly called *Torulopsis glabrata*), *C. parapsilosis*, *C. tropicalis*, *C. pseudotropicalis*, *C. guilliermondii*, *C. dubliniensis*, and *C. lusitaniae*. They cause infections of the mucous membranes, for example, thrush, esophagitis, and vagitits; skin, for example, intertrigo, balanitis, and generalized candidiasis; blood stream infections, for example, candidemia; and deep organ infections, for example, hepatosplenic candidiasis, urinary tract candidiasis, arthritis, endocarditis, and endophthamitis.

Exemplary bacterial pathogens include, but are not limited to, *Aerobacter, Aeromonas, Acinetobacter, Actinomyces israelli, Agrobacterium, Bacillus, Bacillus antracis, Bacteroides, Bartonella, Bordetella, Bortella, Borrelia, Brucella, Burkholderia, Calymmatobacterium, Campylobacter, Citrobacter, Clostridium, Clostridium perfringers, Clostridium tetani, Cornyebacterium, corynebacterium diphtheriae, corynebacterium sp., Enterobacter, Enterobacter aerogenes, Enterococcus, Erysipelothrix rhusiopathiae, Escherichia, Francisella, Fusobacterium nucleatum, Gardnerella, Haemophilus, Hafnia, Helicobacter, Klebsiella, Klebsiella pneumoniae, Lactobacillus, Legionella, Leptospira, Listeria, Morganella, Moraxella, Mycobacterium, Neisseria, Pasteurella, Pasteurella multocida, Proteus, Providencia, Pseudomonas, Rickettsia, Salmonella, Serratia, Shigella, Staphylococcus, Stentorophomonas, Streptococcus, Strepto-*

*bacillus moniliformis, Treponema, Treponema pallidium, Treponema pertenue, Xanthomonas, Vibrio,* and *Yersinia.*

Examples of human viruses include but are not limited to: Retroviridae (e.g. human immunodeficiency viruses, such as HIV-1 (also referred to as HDTV-III, LAVE or HTLV-III/ LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus).

Treatment of Neoplasia

Agents that reduce Helios expression or biological activity (e.g., siRNAs, shRNAs antisense polynucleotides, Helios antagonists) also reduce Treg suppressive activity. Such agents are useful for enhancing an immune response for the treatment of neoplasia. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as acoustic neuroma, acute leukemia, acute lymphocytic leukemia, acute monocytic leukemia, acute myeloblastic leukemia, acute myelocytic leukemia, acute myelomonocytic leukemia, acute promyelocytic leukemia, acute erythroleukemia, adenocarcinoma, angiosarcoma, astrocytoma, basal cell carcinoma, bile duct carcinoma, bladder carcinoma, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, colon cancer, colon carcinoma, craniopharyngioma, cystadenocarcinoma, embryonal carcinoma, endotheliosarcoma, ependymoma, epithelial carcinoma, Ewing's tumor, glioma, heavy chain disease, hemangioblastoma, hepatoma, Hodgkin's disease, large cell carcinoma, leiomyosarcoma, liposarcoma, lung cancer, lung carcinoma, lymphangioendotheliosarcoma, lymphangiosarcoma, macroglobulinemia, medullary carcinoma, medulloblastoma, melanoma, meningioma, mesothelioma, myxosarcoma, neuroblastoma, non-Hodgkin's disease, oligodendroglioma, osteogenic sarcoma, ovarian cancer, pancreatic cancer, papillary adenocarcinomas, papillary carcinoma, pinealoma, polycythemia vera, prostate cancer, rhabdomyosarcoma, renal cell carcinoma, retinoblastoma, schwannoma, sebaceous gland carcinoma, seminoma, small cell lung carcinoma, squamous cell carcinoma, sweat gland carcinoma, synovioma, testicular cancer, uterine cancer, Waldenstrom's fibrosarcoma, and Wilm's tumor.

Anti-Neoplasia Vaccines

Therapeutic compositions that reduce Treg suppressive activity are useful alone or in combination with conventional therapies for the treatment of neoplasia. In one embodiment, a therapeutic agent delineated herein is useful to enhance the efficacy of an anti-neoplasia vaccines. Vaccines comprising tumor antigens are useful as therapeutics for the treatment of various types of neoplasia. Advantageously, these vaccines may be tailored to treat the cancers of particular individuals, by generating vaccines that target specific tumor antigens expressed on a tumor in a subject. Methods of the invention are particularly useful because they provide methods for increasing the efficacy of an immune response against a tumor antigen. Neoplasia vaccines typically contain inactivated tumor cells or tumor antigens that stimulate a patient's immune system. The immune system responds to this stimulation by generating immunoresponsive cells that target the neoplasia. As described herein, $CD25^+$ $CD4^+$ regulatory T cells act to suppress an immune response. In some cases, this suppressive activity is undesirable. The invention provides methods for enhancing the efficacy of an immune response against a vaccine or other immunogenic composition comprising a tumor antigen. Unlike vaccines for other disease that prevent the occurrence of the disease, cancer vaccines are typically administered after a subject has been identified as having a neoplasia.

Anti-neoplasia vaccines are produced using standard methods known in the art. Such vaccines contain tumor-specific antigens—proteins displayed on a tumor cell—capable of stimulating the immune system. By injecting these antigens into a subject, the immune system produces antibodies or cytotoxic T lymphocytes to attack cancer cells that carry that specific antigen. Multiple antigens can be used in this type of vaccine to vary the immune system response. The invention provides therapeutic compositions and methods that may be used alone or in combination with an anti-neoplasia vaccine for the treatment of neoplasia in a subject.

Agents that Disrupt Helios/FoxP3 Interaction

Agents that selectively bind a Helios polypeptide and disrupt Helios binding to a FoxP3 promoter are useful in the methods of the invention. Binding to the Helios polypeptide reduces Helios biological activity as assayed by analyzing binding to the FoxP3 promoter, FoxP3 expression, or Treg suppressive activity. In one embodiment, the invention provides aptamers capable of binding to a Helios polypeptide and disrupting a Helios/FoxP3 interaction. In other embodiments, the invention provides antibodies and antibody fragments useful for disrupting a Helios/FoxP3 interaction.

Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. F(ab')2, and Fab fragments that lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

In other embodiments, the invention provides peptide, such as a fragment of a Helios polypeptide, or a peptide derivative that is capable of binding to a FoxP3 promoter and reducing binding of an endogenous Helios polypeptide. In one embodiment, the peptide comprises a Helios DNA binding domain. Preferably, the peptide competes with an endogenous Helios polypeptide for binding to a FoxP3 promoter. If desired, such peptides comprise a protein transduction domain (e.g., a TAT domain) that facilitates passage across the cell membrane. The invention further provides peptide derivatives (e.g., peptidomimetics), which include cyclic peptides, peptides obtained by substitution of a natural amino acid residue by the corresponding D-stereoisomer, or by a unnatural amino acid residue, chemical derivatives of the peptides, dual peptides, multimers of the peptides, and peptides fused to other proteins or carriers. In one example, a peptide derivative is more resistant to proteolytic degradation than the corresponding non-derivatized peptide. For example, a peptide derivative having D-amino acid substitution(s) in place of one or more L-amino acid residue(s) resists proteolytic cleavage. In another example, the peptide derivative has increased permeability across a cell membrane as compared to the corresponding non-derivatized peptide. For example, a peptide derivative may have a lipophilic moiety coupled at the amino terminus and/or carboxyl terminus and/or an internal site. Such derivatives are highly preferred when targeting intracellular protein-protein interactions, provided they retain the desired functional activity. In another example, a peptide derivative binds with increased affinity to a ligand (e.g., a helios binding site on the FoxP3 promoter).

The peptides or peptide derivatives of the invention are obtained by any method of peptide synthesis known to those skilled in the art, including synthetic and recombinant techniques. For example, the peptides or peptide derivatives can be obtained by solid phase peptide synthesis. Such solid phase syntheses have been described, for example, by Merrifield, J. Am. Chem. Soc. 85:2149, 1964; Vale et al., Science 213:1394-1397, 1984; Marki et al., J. Am. Chem. Soc. 10:3178, 1981, and in U.S. Pat. Nos. 4,305,872 and 4,316,891. Desirably, an automated peptide synthesizer is employed.

Purification of the synthesized peptides or peptide derivatives is carried out by standard methods, including chromatography (e.g., ion exchange, affinity, and sizing column chromatography), centrifugation, differential solubility, hydrophobicity, or by any other standard technique for the purification of proteins. In one embodiment, thin layer chromatography is employed. In another embodiment, reverse phase HPLC (high performance liquid chromatography) is employed.

Polynucleotide Therapy

Polynucleotide therapy is another therapeutic approach in which polynucleotides encoding a Helios polypeptide are introduced into cells (e.g., Tregs). In one approach, where Treg are preventing an immune response in a chronic infection or in cancer Tregs are depleted by over-expressing Helios in these cells. In one embodiment, over-expression of Helios is used to specifically deplete T regs. In another embodiment, the over-expression is used to specifically induce cell death in Tregs. The transgene is delivered to cells in a form in which it can be taken up and expressed in an effective amount to modulate an undesirable immune response. In particular, an increase in Helios expression is desirable to enhance Treg suppressive activity. Transducing retroviral, adenoviral, lentiviral or human immunodeficiency viral (HIV) vectors are used for somatic cell gene therapy because of their high efficiency of infection and stable integration and expression (see, for example, Cayouette et al., Hum. Gene Ther., 8:423-430, 1997; Kido et al., Curr. Eye Res. 15:833-844, 1996; Bloomer et al., J. Virol. 71:6641-6649, 1997; Naldini et al., Science 272:263-267, 1996; Miyoshi et al., Proc. Natl. Acad. Sci. USA, 94:10319-10323, 1997). For example, Helios nucleic acid, or portions thereof, can be cloned into a retroviral vector and driven from its endogenous promoter, from the retroviral long terminal repeat, or from a promoter specific for the target cell type of interest (such as epithelial carcinoma cells). Other viral vectors that can be used include, but are not limited to, adenovirus, adeno-associated virus, vaccinia virus, bovine papilloma virus, vesicular stomatitus virus, or a herpes virus such as Epstein-Barr Virus.

Gene transfer can be achieved using non-viral means requiring infection in vitro. This would include calcium phosphate, DEAE-dextran, electroporation, and protoplast fusion. Liposomes may also be potentially beneficial for delivery of DNA into a cell. Although these methods are available, many of these are of lower efficiency.

Combination Therapies

Therapeutic agents of the invention may be administered alone or in combination with any other standard therapy. In one embodiment, an agent that enhances an immune response (i.e., that reduces Treg suppressive activity) is administered in combination with a standard therapy for neoplasia. Such methods are known to the skilled artisan (e.g., Wadler et al., Cancer Res. 50:3473-86, 1990), and include, but are not limited to, chemotherapy, hormone therapy, immunotherapy, radiotherapy, and any other therapeutic method used for the treatment of neoplasia. In one embodiment, an siRNA, shRNA, antisense RNA, or other agent that reduces Helios expression or biological activity is administered in combination with a cancer vaccine.

In another approach, an agent that enhances an immune response against a pathogen is administered in combination with a conventional therapy for pathogen infection. Such therapies include antibiotics or therapeutic vaccines for the treatment or prevention of a pathogen infection. In still other embodiments, compositions and methods of the invention are used in combination with standard therapies for autoimmune or inflammatory diseases and disorders. Such therapies include, but are not limited to, steroid treatment, Anti-TNF antibodies or soluble TNF agents, monoclonal antibodies against B cells, and immunosuppressive drugs like methotrexate, imuran, and others.

Pharmaceutical Compositions

The pharmaceutical compositions of the present invention comprises agents of the invention useful for modulating an immune response. The pharmaceutical compositions are prepared using methods known in the art and described herein. Methods well known in the art for making compositions and formulations are found, for example, in "Remington: The Science and Practice of Pharmacy," (20th ed., ed. A. R. Gennaro, 2000, Lippincott Williams & Wilkins, Philadelphia).

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilisers, wetting and/or emulsifying agents, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, poly vinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of anti oxidants, for example, vitamins E, .beta.-carotene, or 3,5-di-tert-butyl-4-hydroxytoluene. The alcohol component of those fatty acid esters has a maximum of 6 carbon atoms and is a mono- or polyhydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (poly oxyethylene glycerol trioleate, Gattefoss, Paris), "Miglyol 812" (triglyceride of saturated fatty acids with a chain length of $C_8$ to $C_{12}$, Huls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, drage cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinyl-pyrrolidone, and/or, if desired, disintegrates, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Drage cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or drage coatings or the capsule casings, for example for identification purposes or to indicate different doses of active ingredient.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, drages, tablets or capsules.

The formulations can be administered to human patients in a therapeutically effective amount (e.g., an amount that decreases, suppresses, attenuates, diminishes, arrests, or stabilizes the development or progression of a disease, disorder, or infection in a eukaryotic host organism). The preferred dosage of therapeutic agent to be administered is likely to depend on such variables as the type and extent of the disorder, the overall health status of the particular patient, the formulation of the agent excipients, and its route of administration.

For any of the methods of application described above, an agent that interacts with a helios polypeptide may be applied to the site of the needed therapeutic event (for example, by injection, e.g., direct injection into one or more tumors), or to tissue in the vicinity of the predicted therapeutic event or to a blood vessel supplying the cells predicted to require enhanced therapy. A nucleobase oligomer of the invention, or other regulator of helios biological activity may be administered within a pharmaceutically-acceptable diluent, carrier, or excipient, in unit dosage form. Conventional pharmaceutical practice may be employed to provide suitable formulations or compositions to administer the agents to patients suffering from a disease that is caused by excessive cell proliferation. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the agents. Other potentially useful parenteral delivery systems for agents include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. The preferred dosage of a nucleobase oligomer of the invention is likely to depend on such variables as the type and extent of the disorder, the overall health status of the particular patient, the formulation of the agent excipients, and its route of administration.

As described above, if desired, treatment with an agent of the invention may be combined with therapies for the treatment of proliferative disease (e.g., radiotherapy, surgery, or chemotherapy).

Therapy

Therapy may be provided wherever anti-neoplasia, anti-pathogen, autoimmune, or anti-inflammatory therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. As used herein, the terms "cancer" or "neoplasm" or "neoplastic cells" is meant a collection of cells multiplying in an abnormal manner. Cancer growth is uncontrolled and progressive, and occurs under conditions that would not elicit, or would cause cessation of, multiplication of normal cells.

Identification of Agents that Modulate Helios Biological Activity

Agents that modulate an immune response are identified by exploiting assays described herein. Agents that alter Helios interactions (e.g., binding to FoxP3 promoter) and/or Helios biological activity are exploited in high throughput assays for the purpose of identifying agents that modulate Helios protein-nucleic acid interactions. Compounds that disrupt or inhibit Helios binding to FoxP3 or that otherwise inhibit Helios biological activity (e.g., Helios transcriptional regulatory activity) may be identified by such assays. In addition, compounds that modulate the expression or stability of a Helios polypeptide or nucleic acid molecule may also be identified.

Any number of methods are available for carrying out screening assays to identify new candidate agents that alter the expression of a Helios nucleic acid molecule. In one example, candidate agents are added at varying concentrations to the culture medium of cultured cells expressing a nucleic acid sequences of the invention. Gene expression is then measured, for example, by microarray analysis, Northern blot analysis (Ausubel et al., supra), or RT-PCR, using any appropriate fragment prepared from the nucleic acid molecule as a hybridization probe. The level of gene expression in the presence of the candidate agent is compared to the level measured in a control culture medium lacking the candidate molecule. An agent which modulates the expression of a Helios gene or a functional equivalent thereof, is considered useful in the invention; such a molecule may be used, for example, as a therapeutic to modulate an immune response in a human patient.

In another example, the effect of candidate agents is measured at the level of Helios polypeptide production using the same general approach and standard immunological techniques, such as Western blotting or immunoprecipitation with an antibody specific for a polypeptide encoded by a Helios gene. For example, immunoassays may be used to detect or monitor the expression of at least one of the polypeptides of the invention in a cell. Polyclonal or monoclonal antibodies (produced as described above) that are capable of binding to such a polypeptide may be used in any standard immunoassay format (e.g., ELISA, Western blot, or RIA assay) to measure the level of the Helios polypeptide. In some embodiments, a compound that modulates the expression or biological activity of the Helios polypeptide is considered particularly useful. Again, such a molecule may be used, for example, as a therapeutic to delay, ameliorate, or treat a neoplasia in a human patient or to otherwise modulate an immune response.

In yet another example, candidate compounds may be screened for those that specifically bind to a polypeptide encoded by an Helios gene. The efficacy of such a candidate compound is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate compound may be tested in vitro for its ability to specifically bind a Helios polypeptide of the invention. In another embodiment, a candidate compound is tested for its ability to modulate the biological activity of a Helios polypeptide described herein. The biological activity of a Helios polypeptide may be assayed using any standard method, for example, FoxP3 binding, or modulation to T cell suppressive activity.

In another working example, a polynucleotide described herein (e.g., a Helios nucleic acid molecule) is expressed as a transcriptional or translational fusion with a detectable reporter, and expressed in an isolated cell (e.g., mammalian or insect cell). The cell expressing the fusion protein is then contacted with a candidate compound, and the expression of the detectable reporter in that cell is compared to the expression of the detectable reporter in an untreated control cell. A candidate compound that alters (increases or decreases) the expression of the detectable reporter is a compound that is useful for modulation of an immune response. Agents that increase Helios expression are useful for reducing an undesirable immune response (e.g., autoimmunity, inflammatory disease). Agents that reduce Helios expression are useful for reducing T cell suppressive activity. Such agents are useful for the treatment of a neoplasia or for enhancing a desirable immune response (e.g., an immune response against a pathogen).

In one particular example, a candidate compound that binds to a Helios polypeptide may be identified using a chromatography-based technique. For example, a recombinant polypeptide of the invention may be purified by standard techniques from cells engineered to express the polypeptide and may be immobilized on a column. A solution of candidate compounds is then passed through the column, and a compound specific for the Helios polypeptide is identified on the basis of its ability to bind to the polypeptide and be immobilized on the column. To isolate the compound, the column is washed to remove non-specifically bound molecules, and the compound of interest is then released from the column and collected. Similar methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to modulate the activity of a Helios polypeptide (e.g., as described herein). Compounds isolated by this approach may also be used, for example, as therapeutics to treat a modulate an immune response in a human patient. Compounds that are identified as binding to a polypeptide of the invention with an affinity constant less than or equal to 10 mM are considered particularly useful in the invention. Alternatively, any in vivo protein interaction detection system, for example, any two-hybrid assay may be utilized.

Potential Helios agonists and antagonists include organic molecules, peptides, peptide mimetics, polypeptides, nucleic acid molecules, and antibodies that bind to a nucleic acid sequence or polypeptide of the invention (e.g., a Helios polypeptide or nucleic acid molecule or a FoxP3 promoter site).

Each of the DNA sequences listed herein may also be used in the discovery and development of a therapeutic compound for the treatment of neoplasia. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct sequences that promote the expression of the coding sequence of interest. Such sequences may be isolated by standard techniques (Ausubel et al., supra).

Small molecules of the invention preferably have a molecular weight below 2,000 daltons, more preferably between 300 and 1,000 daltons, and most preferably between 400 and 700 daltons. It is preferred that these small molecules are organic molecules.

Test Extracts and Compounds

In general, compounds that modulate Helios expression or biological activity (e.g., Helios transcriptional regulatory activity) are identified from large libraries of both natural products, synthetic (or semi-synthetic) extracts or chemical libraries, according to methods known in the art. In one embodiment, a selected compound decreases Helios expression or biological activity to reduce Treg suppressive activity, thereby enhancing a desirable immune response (e.g., an immune response against a tumor antigen, pathogen). In another embodiment, a selected compound increases Helios expression or biological activity to enhance Treg suppressive activity, thereby reducing an undesirable immune response (e.g., autoimmunity, inflammatory disease).

Those skilled in the art will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from, for example, Brandon Associates (Merrimack, N.H.), Aldrich Chemical (Milwaukee, Wis.), and Talon Cheminformatics (Acton, Ont.)

Alternatively, libraries of natural compounds in the form of bacterial, fungal, plant, and animal extracts are commercially available from a number of sources, including, but not limited to, Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art (e.g., by combinatorial chemistry methods or standard extraction and fractionation methods). Furthermore, if desired, any library or compound may be readily modified using standard chemical, physical, or biochemical methods.

The present invention provides methods of treating disease and/or disorders or symptoms thereof which comprise administering a therapeutically effective amount of a pharmaceutical composition comprising a compound of the formulae herein to a subject (e.g., a mammal, such as a human). Thus, one embodiment is a method of treating a subject suffering from or susceptible to a disease or disorder or symptom thereof associated with the disregulation of an immune response. In one embodiment, the disease, disorder or symptom is treated by reducing Treg suppressive activity, thereby enhancing a desirable immune response for the treatment of neoplasia, pathogen infection, or any other pathology where a reduction in Treg suppressive activity is desirable. In another embodiment, the disease, disorder or symptom is treated by increasing Treg suppressive activity, thereby reducing an undesirable immune response for the treatment or autoimmune disease, inflammatory disease, or any other disease characterized by a reduction in Treg suppressive activity. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which disregulation of an immune response may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with disregulation of an immune response, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Kits

The invention also provides kits for the modulation of an immune response. In one embodiment, the kit includes an effective amount of an agent herein (e.g., small compound, polynucleotide, polypeptide) in unit dosage form, together with instructions for administering the compound to a subject suffering from or susceptible to a disease that could benefit from modulation of an immune response. In other embodiments, the kit comprises a sterile container which contains the compound; such containers can be boxes, ampoules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the compound of the formulae herein to modulate an immune response in a subject in need thereof. In other embodiments, the instructions include at least one of the following: description of the compound; dosage schedule and administration for treatment of a neoplasia, a pathogen infection, an autoimmune disease or an inflammatory disease; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Helios is Expressed in Human Treg

To determine whether Helios expression is up-regulated in Treg isolated from the peripheral blood of healthy human donors, Helios expression was evaluated in $CD4^+CD25^+$ T cells. As shown in FIG. 1A, qRT-PCR determination of transcript levels from FACS sorted $CD4^+CD25^-$ or $CD4^+CD25^+$ T cells showed that Helios expression is relatively restricted to the $CD25^+$ compartment of human CD4 T cells, which correlates well with FoxP3+ expression. Transient FoxP3 expression is a property of activated human CD4 T cells (Pillai et al., Clin Immunol. 2007; 123:18-29; Wang et al., Eur J Immunol. 2007; 37:129-138). It was next determined whether up-regulation of Helios precedes FoxP3 up-regulation. As shown in FIG. 1B, Helios message levels reached peak levels 12 hours post-activation, whereas FoxP3 levels appeared to peak approximately 24 hours post-activation. Thus, up-regulation of Helios precedes FoxP3 up-regulation.

Example 2: Induced Expression of Helios in CD4 T Cells Induced Apoptosis

To better elucidate a possible functional relationship between Helios and FoxP3, a series of Helios lentivirus constructs was generated. The viral vectors used were MSCV-IRES GFP vectors. These were used to transduce naïve human CD4 T cells. Initial results suggested poor survival of specifically transduced cells. Therefore, Jurkat T cells were used to specifically test whether Helios affects T cell survival. Cells were transfected with the full-length Helios or a non-DNA binding isoform (as a negative control). Cultures of transfected cells were assayed for apoptosis using 7AAD and Annexin V staining (FIG. 1c) (Zhang et al., Blood 2007; 109:2190-2197). These data showed that ectopic expression of Helios in CD4 T cells induced apoptosis. Taken together these data showed a relative up-regulation of Helios in Treg, but suggested that Helios expression alone was insufficient to generate Treg in vitro.

Example 3: Helios is a Transcriptional Regulator of FoxP3

To explore Helios function in Treg, EL4 thymoma cells were used to determine whether the Helios transcription factor directly interacts with the FoxP3 promoter. EL4 thymoma cells are reported to express multiple isoforms of Helios (Hahm et al., Genes Dev. 1998; 12:782-796). EL4 thymoma cells transcribe FoxP3 upon stimulation with anti-CD3e, anti-CD28, and TGFβ (Tone et al., Nat Immunol. 2008; 9:194-202). Myc-tagged full-length Helios or insert control were over-expressed in EL4 cells, and the cells were cultured overnight. An anti-Myc antibody was able to precipitate regions of the FoxP3 promoter in a ChIP assay 24 hours after stimulation (FIG. 1D). Two separate but adjacent regions (−1184 to −724 and −692 to −335 from transcriptional start site) on the FoxP3 promoter were specifically immunoprecipitated. These data indicate that the DNA binding isoform of Helios is present at the promoter region during FoxP3 transcription in these cells, and further indicate that Helios likely functions in the transcriptional regulation of FoxP3 levels in T cells.

Example 4: Helios Modulates FoxP3 Message Levels and Treg Function

Figures 2A, 2B, 2C, 2D:
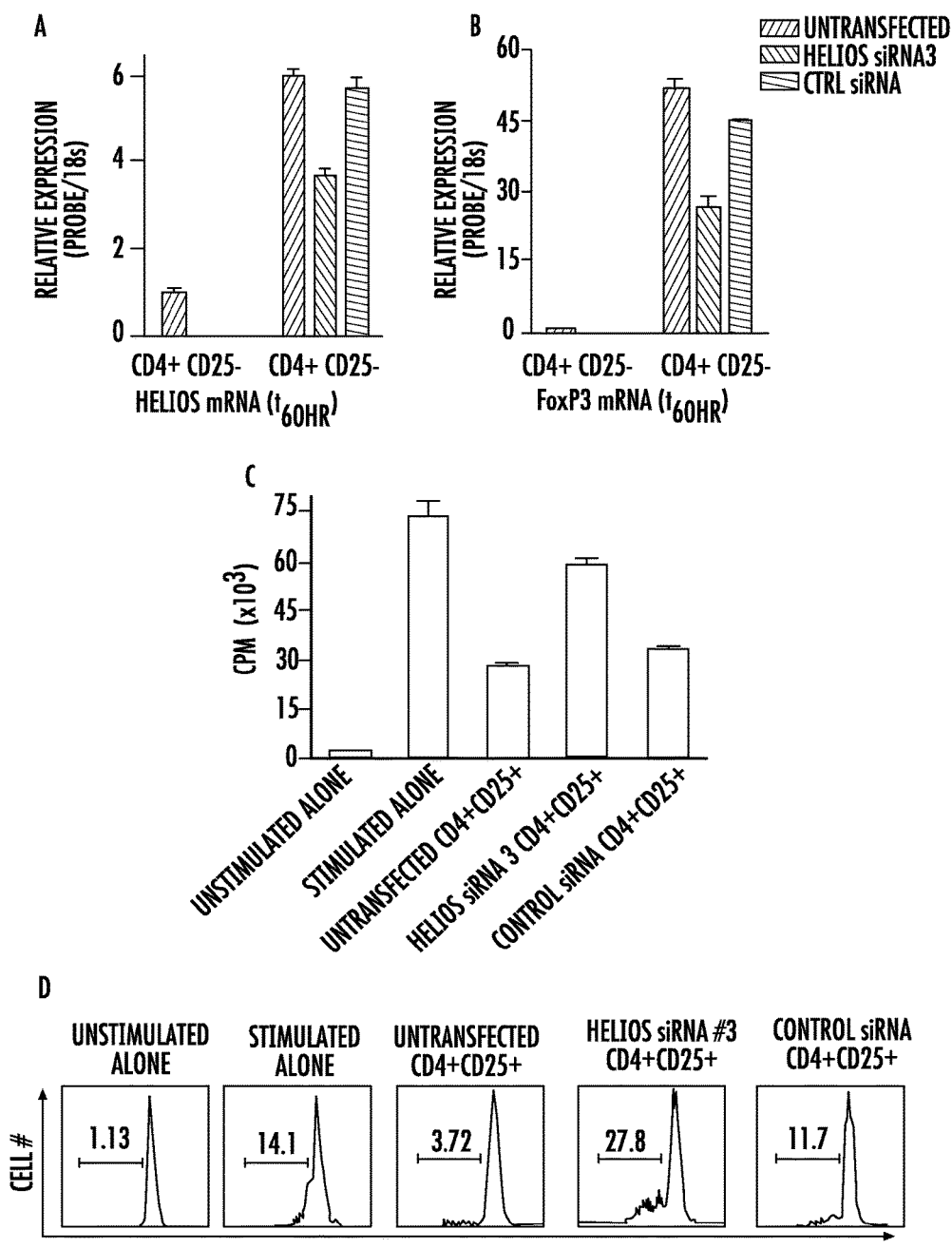
FIGS. 2A-2D show that Helios knockdown results in decreased FoxP3 message and diminished suppressive capacity of human Treg in vitro. Primary CD4$^+$CD25$^+$ T cells were nucleofected with Helios siRNA or control siRNA and incubated for 60 hours.

To further explore a role for Helios in FoxP3 expression, siRNA was used to knockdown Helios expression in CD4$^+$CD25$^+$ Treg. As shown in FIG. 2A, partial Helios knockdown could be achieved. Interestingly, specific Helios knockdown also resulted in diminished FoxP3 transcript levels in these cells (FIG. 2B). Off-target activity of siRNA was ruled out using a panel of siRNA's to target Helios message in CD4$^+$CD25$^+$ T cells. The resultant reduction of FoxP3 through Helios knockdown indicates that Helios regulates FoxP3 expression. Because Helios binds to the FoxP3 promoter and partial reduction of Helios resulted in decreased levels of FoxP3 message, the importance of Helios in Treg function was explored by performing a number of classical in vitro suppression assays (Thornton et al., J Exp Med. 1998; 188:287-296; Ono et al., Nature. 2007; 446:685-689). In these studies, siRNA transfected CD4$^+$CD25$^+$ Treg were co-cultured with autologous CD4$^+$CD25$^-$ T cells (responders). As shown in FIG. 2C, untransfected and control siRNA transfected Tregs suppressed the proliferation of responding cells significantly, but the introduction of Helios siRNA into human regulatory T cells significantly mitigated their suppressive capacity. This assay was performed multiple times, with multiple PBL donors, and with consistent results. In order to eliminate the remote possibility that the proliferation of Helios siRNA transfected cells accounted for increased H$^3$-thymidine incorporation, suppression assays were performed using CFSE-labeled responder cells.

These results (FIG. 2D) were consistent with our H$^3$ incorporation data, confirming that Helios siRNA transfected Treg have diminished suppressive capacity in vitro. Taken together, these data confirm that the Ikaros family member Helios is up-regulated in human Treg. Direct functional studies of Helios' role in CD4 T cells are complicated by the finding that Helios expression alone likely mediates apoptosis. In natural Treg, co-expression of anti-apoptotic proteins such as Bcl-2, might counteract this apoptotic capacity (Liu et al., J Immunol. 2005; 175:7898-7904). On a mechanistic level, Helios binds to at least two sites on the FoxP3 promoter, and siRNA-mediated Helios knockdown attenuates FoxP3 levels. Functionally, Helios knockdown mitigates the suppressive capacity of human Treg—indicating that manipulation of Helios function or levels may be used to attenuate Treg function in settings such as tumor immunotherapy, where enhanced immunity is desired.

The results reported herein were obtained using the following methods and materials.

Lymphocyte Isolation.

Lymphocytes were purified from healthy donors under an Institutional Review Board (IRB)-approved protocol. Peripheral blood cells were separated via density centrifugation on Ficoll gradient (GE Healthcare). The human regulatory T cell isolation kit (Mylteni Biotec) was used according to manufacturer's instruction to enrich CD4 T cells prior to Fluorescence Activated Cell Sorting (FACS).

Cell Lines and Transfections.

EL4 and Jurkat T cells were maintained in Jurkat/EL4 media (RPMI, 10% FCS, and antibiotics). Both cell lines were electroporated at 280V, 975 uF, and 335 R settings using Equibio Easyject Electorporator (Wolf laboratories). Post-electroporation, cells were placed immediately in antibiotic free media supplemented with 20% FCS and rested for 12 hours before additional studies.

Apoptosis.

Apoptosis was quantified using the Apoptosis kit (BD). Jurkat cells exposed to UV light serves as a positive control.

ChIP Assay.

The chromatin-immunoprecipitation assay kit (Upstate-Millipore) was used according to the manufacturer's instructions with minor modifications. Briefly, EL4 cells were transfected with indicated constructs, rested overnight, and stimulated with anti-CD3e (5 ug/mL, immobilized), anti-CD28 (1 ug/mL, soluble), and TGF β (2 ng/mL) for twenty-four hours. Cells were fixed, lysed with 1% SDS, sonicated, Micrococcal nuclease (New England Biolabs) treated, and immunoprecipitated. The following FoxP3 primer pairs were used:

```
                                        (SEQ ID NO: 6)
Fwd     5'-actttctcttcctcaggcct-3'
and (SEQ ID NO: 7)
Rvs     5'-ctgtcataattttggtagcc-3';

(SEQ ID NO: 8)
Fwd     5'-cttttctttttacacggaatctgg-3';
and (SEQ ID NO: 9)
Rvs     5'-cccccacaaattcacagaat-3';

(SEQ ID NO: 10)
Fwd     5'-cttttttctccatgaattgc-3'
and (SEQ ID NO: 11)
Rvs     5'-ctcatgagaaaccacaatttt-3';

(SEQ ID NO: 12)
Fwd     5'-gatttgacttattttccctc-3'
and (SEQ ID NO: 13)
Rvs     5' gcttttataccgagaagaaa-3'.
```

In Vitro Suppression Assay.

Purified CD4$^+$CD25$^+$ T cells were nucelofected with siRNA (Ambion) using Amaxa kits (Amaxa).

The human sequence is siRNA duplex. Sense: CCUCA-CAAGUGCAACUACUtt (SEQ ID NO: 1); Antisense: AGUAGUUGCACUUGUGAGGtt (SEQ ID NO: 2).

The mouse siRNA sequences are in a standard pLKO.1-GFP construct and here are the 5 siRNA sequences Sense-loop-antisense sequences.

```
                                        (SEQ ID NO: 14)
1) CCGGCTCGATTCTACTGACTCAGAACTCGAGTTCTGAGTCAGTAGAAT

CGAGTTTTTG (SEQ ID NO: 15)
2) CCGGCCTATCATGGACAACAATATTCTCGAGAATATTGTTGTCCATGA

TAGGTTTTTG
```

```
                                                          (SEQ ID NO: 16)
3) CCGGGCCTTAAATCCCAAGAGGAAACTCGAGTTTCCTCTTGGGATTTA

AGGCTTTTTG (SEQ ID NO: 17)
4) CCGGCGATTCAGCTACCCAGATATTCTCGAGAATATCTGGGTAGCTGA

ATCGTTTTTG (SEQ ID NO: 18)
5) CCGGCGTCACTTTATCAGCATTCAACTCGAGTTGAATGCTGATAAAGT

GACGTTTTTG
```

After nucleofection, cells were incubated for 60 hours in complete RPMI supplemented with 10% autologous serum. For suppression assays, irradiated (8000 rad) feeder cells were admixed with CD4+ CD25− T cell responders and CD4+CD25+T cell suppressors in 2:1:1 ratio in serum free media for 5 days. Proliferation was assayed as described previously (Huang et al., Immunity. 2004; 21:503-513). In some assays, responders were CFSE labeled, and division quantified by CFSE dilution.

Quantitative PCR.

qRT-PCR was performed as previously described (Huang et al., Immunity. 2004; 21:503-513). All primers and probes for quantitative RT-PCR were obtained from Applied Biosystems.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for increasing an effector T cell-mediated immune response, the method comprising contacting one or more cells with an inhibitory nucleic acid molecule that reduces Helios expression or biological activity, and reduces Treg CD4+CD25+T lymphocyte suppression of an effector T cell mediated immune response.

2. The method of claim 1, wherein the inhibitory nucleic acid molecule is selected from the group consisting of siRNA, shRNA, or antisense oligonucleotide.

3. The method of claim 1, wherein the inhibitory nucleic acid molecule disrupts Helios binding to a FoxP3 promoter.

4. The method of claim 3, wherein the inhibitory nucleic acid molecule specifically binds a Helios polypeptide.

5. The method of claim 3, wherein the inhibitory nucleic acid molecule binds the FoxP3 promoter at about nucleotides −1184 to −724 and/or −692 to −335 from transcriptional start site.

6. A method for increasing an effector T cell-mediated immune response in a subject in need thereof, the method comprising administering to the subject an effective amount of an inhibitory nucleic acid molecule that reduces Helios expression or biological activity, and reduces Treg CD4+CD25+T lymphocyte suppression of an effector T cell mediated immune response in the subject.

7. The method of claim 6, wherein the subject is identified as having a neoplasia or pathogen infection.

8. The method of claim 6, wherein the subject is identified as having an autoimmune or inflammatory disease.

9. The method of claim 6, further comprising administering to the subject an immunogenic composition comprising a tumor antigen.

10. The method of claim 9, wherein the method enhances an immune response against a tumor antigen.

11. The method of claim 6, wherein the polynucleotide is an inhibitory nucleic acid molecule selected from the group consisting of siRNA, shRNA, or antisense oligonucleotide.

12. The method of claim 6, wherein the inhibitory nucleic acid molecule is an that specifically disrupts Helios binding to a FoxP3 promoter.

13. The method of claim 6, wherein the inhibitory nucleic acid molecule binds the FoxP3 promoter at about nucleotides −1184 to −724 and/or −692 to −335 from transcriptional start site and disrupts a Helios/FoxP3 interaction.

14. A method for increasing the efficacy of an antineoplasia vaccine in a subject, the method comprising administering to the subject a vaccine comprising a tumor antigen and an inhibitory nucleic acid molecule that reduces the level or activity of a Helios polypeptide, and reduces Treg CD4+CD25+T lymphocyte suppression of an effector T cell mediated immune response in a cell of the subject.

15. The method of claim 14, wherein the inhibitory nucleic acid molecule is a Helios inhibitory nucleic acid molecule selected from the group consisting of an siRNA, shRNA, or antisense oligonucleotide.

16. The method of claim 15, wherein the Helios inhibitory nucleic acid molecule is a siRNA having the following nucleic acid sequence:

```
                                            (SEQ ID NO: 1)
Sense:      CCUCACAAGUGCAACUACUtt (SEQ ID NO: 2)
Antisense:  AGUAGUUGCACUUGUGAGGtt.
```

17. The method of claim 5, wherein the inhibitory nucleic acid molecule is a siRNA having the following nucleic acid sequence:

Sense:
(SEQ ID NO: 1)
CCUCACAAGUGCAACUACUtt

Antisense:
(SEQ ID NO: 2)
AGUAGUUGCACUUGUGAGGtt.

18. The method of claim 11, wherein the inhibitory nucleic acid molecule is a siRNA having the following nucleic acid sequence:

Sense:
(SEQ ID NO: 1)
CCUCACAAGUGCAACUACUtt

Antisense:
(SEQ ID NO: 2)
AGUAGUUGCACUUGUGAGGtt.

* * * * *

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: synthetic sequence

<400> SEQUENCE: 1
ccucacaagu gcaacuacut t                                         21

<210> SEQ ID NO 2
<211> LENGTH: 21
<212> TYPE: DNA
<213> ORGANISM: Artificial Sequence
<220> FEATURE:
<223> OTHER INFORMATION: synthetic sequence

<400> SEQUENCE: 2
aguaguugca cuugugaggt t                                         21

<210> SEQ ID NO 3
<211> LENGTH: 526
<212> TYPE: PRT
<213> ORGANISM: Homo sapiens

<400> SEQUENCE: 3

Met Glu Thr Asp Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Lys Pro
    50                  55                  60

Leu Ser Arg Glu Asn Glu Ile Arg Gly His Asp Glu Gly Ser Ser Leu
65                  70                  75                  80
```

-continued

```
Glu Glu Pro Leu Ile Glu Ser Ser Glu Val Ala Asp Asn Arg Lys Val
                 85                  90                  95
Gln Glu Leu Gln Gly Glu Gly Gly Ile Arg Leu Pro Asn Gly Lys Leu
            100                 105                 110
Lys Cys Asp Val Cys Gly Met Val Cys Ile Gly Pro Asn Val Leu Met
        115                 120                 125
Val His Lys Arg Ser His Thr Gly Glu Arg Pro Phe His Cys Asn Gln
130                 135                 140
Cys Gly Ala Ser Phe Thr Gln Lys Gly Asn Leu Leu Arg His Ile Lys
145                 150                 155                 160
Leu His Ser Gly Glu Lys Pro Phe Lys Cys Pro Phe Cys Ser Tyr Ala
                165                 170                 175
Cys Arg Arg Arg Asp Ala Leu Thr Gly His Leu Arg Thr His Ser Val
            180                 185                 190
Gly Lys Pro His Lys Cys Asn Tyr Cys Gly Arg Ser Tyr Lys Gln Arg
        195                 200                 205
Ser Ser Leu Glu Glu His Lys Glu Arg Cys His Asn Tyr Leu Gln Asn
    210                 215                 220
Val Ser Met Glu Ala Ala Gly Gln Val Met Ser His His Val Pro Pro
225                 230                 235                 240
Met Glu Asp Cys Lys Glu Gln Glu Pro Ile Met Asp Asn Asn Ile Ser
                245                 250                 255
Leu Val Pro Phe Glu Arg Pro Ala Val Ile Glu Lys Leu Thr Gly Asn
            260                 265                 270
Met Gly Lys Arg Lys Ser Ser Thr Pro Gln Lys Phe Val Gly Glu Lys
        275                 280                 285
Leu Met Arg Phe Ser Tyr Pro Asp Ile His Phe Asp Met Asn Leu Thr
    290                 295                 300
Tyr Glu Lys Glu Ala Glu Leu Met Gln Ser His Met Met Asp Gln Ala
305                 310                 315                 320
Ile Asn Asn Ala Ile Thr Tyr Leu Gly Ala Glu Ala Leu His Pro Leu
                325                 330                 335
Met Gln His Pro Pro Ser Thr Ile Ala Glu Val Ala Pro Val Ile Ser
            340                 345                 350
Ser Ala Tyr Ser Gln Val Tyr His Pro Asn Arg Ile Glu Arg Pro Ile
        355                 360                 365
Ser Arg Glu Thr Ala Asp Ser His Glu Asn Asn Met Asp Gly Pro Ile
    370                 375                 380
Ser Leu Ile Arg Pro Lys Ser Arg Pro Gln Glu Arg Glu Ala Ser Pro
385                 390                 395                 400
Ser Asn Ser Cys Leu Asp Ser Thr Asp Ser Glu Ser Ser His Asp Asp
                405                 410                 415
His Gln Ser Tyr Gln Gly His Pro Ala Leu Asn Pro Lys Arg Lys Gln
            420                 425                 430
Ser Pro Ala Tyr Met Lys Glu Asp Val Lys Ala Leu Asp Thr Thr Lys
        435                 440                 445
Ala Pro Lys Gly Ser Leu Lys Asp Ile Tyr Lys Val Phe Asn Gly Glu
    450                 455                 460
Gly Glu Gln Ile Arg Ala Phe Lys Cys Glu His Cys Arg Val Leu Phe
465                 470                 475                 480
Leu Asp His Val Met Tyr Thr Ile His Met Gly Cys His Gly Tyr Arg
                485                 490                 495
```

| Asp | Pro | Leu | Glu | Cys | Asn | Ile | Cys | Gly | Tyr | Arg | Ser | Gln | Asp | Arg | Tyr |
|-----|-----|-----|-----|-----|-----|-----|-----|-----|-----|-----|-----|-----|-----|-----|-----|
|     |     |     | 500 |     |     |     | 505 |     |     |     |     | 510 |     |     |     |

| Glu | Phe | Ser | Ser | His | Ile | Val | Arg | Gly | Glu | His | Thr | Phe | His |
|-----|-----|-----|-----|-----|-----|-----|-----|-----|-----|-----|-----|-----|-----|
|     | 515 |     |     |     |     | 520 |     |     |     |     | 525 |     |     |

<210> SEQ ID NO 4
<211> LENGTH: 2397
<212> TYPE: DNA
<213> ORGANISM: Homo sapiens

<400> SEQUENCE: 4

| | | | | | |
|---|---|---|---|---|---|
| gcacacactc | atcgaaaaaa | atttggatta | ttagaagaga | gaggtctgcg | gcttccacac | 60 |
| cgtacagcgt | ggttttttctt | ctcggtataa | aagcaaagtt | gttttttgata | cgtgacagtt | 120 |
| tcccacaagc | caggctgatc | cttttctgtc | agtccacttc | accaagcctg | cccttggaca | 180 |
| aggacccgat | gcccaacccc | aggcctggca | agccctcggc | ccttccttg | gcccttggcc | 240 |
| catccccagg | agcctcgccc | agctggaggg | ctgcacccaa | agcctcagac | ctgctggggg | 300 |
| cccggggccc | aggggggaacc | ttccaggggcc | gagatcttcg | aggcggggcc | catgcctcct | 360 |
| cttcttcctt | gaaccccatg | ccaccatcgc | agctgcagct | gcccacactg | ccctagtca | 420 |
| tggtggcacc | ctccggggca | cggctgggcc | ccttgcccca | cttacaggca | ctcctccagg | 480 |
| acaggccaca | tttcatgcac | cagctctcaa | cggtggatgc | ccacgccggg | accctgtgc | 540 |
| tgcaggtgca | cccctggag | agcccagcca | tgatcagcct | cacaccaccc | accaccgcca | 600 |
| ctggggtctt | ctccctcaag | gcccggcctg | gcctcccacc | tgggatcaac | gtggccagcc | 660 |
| tggaatgggt | gtccagggag | ccggcactgc | tctgcacctt | cccaaatccc | agtgcaccca | 720 |
| ggaaggacag | cacccttcg | gctgtgcccc | agagctccta | cccactgctg | gcaaatggtg | 780 |
| tctgcaagtg | gcccggatgt | gagaaggtct | tcgaagagcc | agaggacttc | ctcaagcact | 840 |
| gccaggcgga | ccatcttctg | gatgagaagg | gcagggcaca | atgtctcctc | cagagagaga | 900 |
| tggtacagtc | tctggagcag | cagctggtgc | tggagaagga | gaagctgagt | gccatgcagg | 960 |
| cccacctggc | tgggaaaatg | gcactgacca | aggcttcatc | tgtggcatca | tccgacaagg | 1020 |
| gctcctgctg | catcgtagct | gctggcagcc | aaggccctgt | cgtcccagcc | tggtctggcc | 1080 |
| cccgggaggc | ccctgacagc | ctgtttgctg | tccggaggca | cctgtggggt | agccatggaa | 1140 |
| acagcacatt | cccagagttc | ctccacaaca | tggactactt | caagttccac | aacatgcgac | 1200 |
| cccctttcac | ctacgccacg | ctcatccgct | gggccatcct | ggaggctcca | gagaagcagc | 1260 |
| ggacactcaa | tgagatctac | cactggttca | cacgcatgtt | tgccttcttc | agaaaccatc | 1320 |
| ctgccacctg | gaagaacgcc | atccgccaca | acctgagtct | gcacaagtgc | tttgtgcggg | 1380 |
| tggagagcga | gaagggggct | gtgtggaccg | tggatgagct | ggagttccgc | aagaaacgga | 1440 |
| gccagaggcc | cagcaggtgt | tccaacccta | cacctggccc | ctgacctcaa | gatcaaggaa | 1500 |
| aggaggatgg | acgaacaggg | gccaaactgg | tgggaggcag | aggtggtggg | ggcagggatg | 1560 |
| ataggccctg | gatgtgccca | cagggaccaa | gaagtgaggt | ttccactgtc | ttgcctgcca | 1620 |
| gggcccctgt | tcccccgctg | gcagccaccc | cctcccccat | catatccttt | gccccaaggc | 1680 |
| tgctcagagg | ggccccggtc | ctggccccag | ccccacctc | cgcccagac | acaccccca | 1740 |
| gtcgagccct | gcagccaaac | agagccttca | aaccagcca | cacagagcct | gcctcagctg | 1800 |
| ctcgcacaga | ttacttcagg | gctggaaaag | tcacacagac | acacaaaatg | tcacaatcct | 1860 |
| gtccctcact | caacacaaac | cccaaaacac | agagagcctg | cctcagtaca | ctcaaacaac | 1920 |
| ctcaaagctg | catcatcaca | caatcacaca | caagcacagc | cctgacaacc | cacacacccc | 1980 |

-continued

```
aaggcacgca cccacagcca gcctcagggc ccacaggggc actgtcaaca caggggtgtg    2040
cccagaggcc tacacagaag cagcgtcagt accctcagga tctgaggtcc aacacgtgc    2100 tcgctcacac acacggcctg ttagaattca cctgtgtatc tcacgcatat gcacacgcac    2160 agcccccccag tgggtctctt gagtcccgtg cagacacaca cagccacaca cactgccttg    2220
ccaaaaatac cccgtgtctc ccctgccact cacctcactc ccattccctg agccctgatc    2280
catgcctcag cttagactgc agaggaacta ctcatttatt tgggatccaa ggccccccaac    2340 ccacagtacc gtcccccaata aactgcagcc gagctcccca caaaaaaaaa aaaaaa    2397
```

<210> SEQ ID NO 5
<211> LENGTH: 923
<212> TYPE: PRT
<213> ORGANISM: Homo sapiens

<400> SEQUENCE: 5

```
Met Glu Arg Gly Leu Pro Leu Leu Cys Ala Val Leu Ala Leu Val Leu
1               5                   10                  15

Ala Pro Ala Gly Ala Phe Arg Asn Asp Glu Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300
```

```
Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
            325                 330                 335

Thr Ala Val Gly Thr Gln Gly Ala Ile Ser Lys Glu Thr Lys Lys Lys
        340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
                420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
        595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Asn Ser Ala His
705                 710                 715                 720
```

```
Cys Met Thr Phe Trp Tyr His Met Ser Gly Ser His Val Gly Thr Leu
            725                 730                 735

Arg Val Lys Leu Arg Tyr Gln Lys Pro Glu Glu Tyr Asp Gln Leu Val
        740                 745                 750

Trp Met Ala Ile Gly His Gln Gly Asp His Trp Lys Glu Gly Arg Val
    755                 760                 765

Leu Leu His Lys Ser Leu Lys Leu Tyr Gln Val Ile Phe Glu Gly Glu
770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
            805                 810                 815

Lys Lys Asn Pro Glu Ile Lys Ile Asp Glu Thr Gly Ser Thr Pro Gly
        820                 825                 830

Tyr Glu Gly Glu Gly Glu Gly Asp Lys Asn Ile Ser Arg Lys Pro Gly
    835                 840                 845

Asn Val Leu Lys Thr Leu Glu Pro Ile Leu Ile Thr Ile Ile Ala Met
850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
            885                 890                 895

Glu Asn Tyr Asn Phe Glu Leu Val Asp Gly Val Lys Leu Lys Lys Asp
        900                 905                 910

Lys Leu Asn Thr Gln Ser Thr Tyr Ser Glu Ala
    915                 920

<210> SEQ ID NO 6
<211> LENGTH: 20
<212> TYPE: DNA
<213> ORGANISM: Artificial Sequence
<220> FEATURE:
<223> OTHER INFORMATION: synthetic sequence

<400> SEQUENCE: 6
actttctctt cctcaggcct                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic sequene'

<400> SEQUENCE: 7
ctgtcataat tttggtagcc                                              20

<210> SEQ ID NO 8
<211> LENGTH: 25
<212> TYPE: DNA
<213> ORGANISM: Artificial Sequence
<220> FEATURE:
<223> OTHER INFORMATION: synthetic sequence

<400> SEQUENCE: 8
cttttctctt ttacacggaa tctgg                                        25
```

-continued

```
<210> SEQ ID NO 9
<211> LENGTH: 20
<212> TYPE: DNA
<213> ORGANISM: Artificial Sequence
<220> FEATURE:
<223> OTHER INFORMATION: synthetic sequence

<400> SEQUENCE: 9
cccccacaaa ttcacagaat                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic sequence

<400> SEQUENCE: 10
cttttttctc catgaattgc                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic sequence

<400> SEQUENCE: 11
ctcatgagaa accacaattt                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic sequence

<400> SEQUENCE: 12
gatttgactt attttccctc                                              20

<210> SEQ ID NO 13
<211> LENGTH: 20
<212> TYPE: DNA
<213> ORGANISM: Artificial Sequence
<220> FEATURE:
<223> OTHER INFORMATION: synthetic sequence

<400> SEQUENCE: 13
gcttttatac cgagaagaaa                                              20

<210> SEQ ID NO 14
<211> LENGTH: 58
<212> TYPE: DNA
<213> ORGANISM: Mus musculus

<400> SEQUENCE: 14
ccggctcgat tctactgact cagaactcga gttctgagtc agtagaatcg agtttttg    58

<210> SEQ ID NO 15
<211> LENGTH: 58
<212> TYPE: DNA
<213> ORGANISM: Mus musculus

<400> SEQUENCE: 15
ccggcctatc atgacaaca atattctcga gaatattgtt gtccatgata ggttttg      58
```

```
<210> SEQ ID NO 16
<211> LENGTH: 57
<212> TYPE: DNA
<213> ORGANISM: Mus musculus
<220> FEATURE:
<221> NAME/KEY: misc_feature
<222> LOCATION: (54)..(55)
<223> OTHER INFORMATION: n is a, c, g, t or u

<400> SEQUENCE: 16
ccgggcctta atcccaaga ggaaactcga gtttcctctt gggatttaag gctnntg      57

<210> SEQ ID NO 17
<211> LENGTH: 58
<212> TYPE: DNA
<213> ORGANISM: Mus musculus

<400> SEQUENCE: 17
ccggcgattc agctacccag atattctcga gaatatctgg gtagctgaat cgttttg     58

<210> SEQ ID NO 18
<211> LENGTH: 57
<212> TYPE: DNA
<213> ORGANISM: Mus musculus
<220> FEATURE:
<221> NAME/KEY: misc_feature
<222> LOCATION: (12)..(12)
<223> OTHER INFORMATION: n is a, c, g, t or u

<400> SEQUENCE: 18
ccggcgtcac tnatcagcat tcaactcgag ttgaatgctg ataaagtgac gtttttg     57
```